(12) United States Patent
McAuliffe et al.

(10) Patent No.: US 7,179,932 B2
(45) Date of Patent: Feb. 20, 2007

(54) SYNTHESIS OF CIS-DIOLS FROM ARYL SILANES

(75) Inventors: Joseph C. McAuliffe, Sunnyvale, CA (US); Gregory M. Whited, Belmont, CA (US); Wyatt Charles Smith, Tiburon, CA (US)

(73) Assignee: Genencor International, Inc., Palo Alto, CA (US)

( * ) Notice: Subject to any disclaimer, the term of this patent is extended or adjusted under 35 U.S.C. 154(b) by 429 days.

(21) Appl. No.: 10/453,468

(22) Filed: Jun. 3, 2003

(65) Prior Publication Data

US 2004/0033574 A1 Feb. 19, 2004

Related U.S. Application Data

(60) Provisional application No. 60/435,187, filed on Dec. 18, 2002, provisional application No. 60/385,373, filed on Jun. 3, 2002.

(51) Int. Cl.
*C07F 7/04* (2006.01)

(52) U.S. Cl. ..................................... 556/449

(58) Field of Classification Search ................. 556/449
See application file for complete search history.

(56) References Cited

U.S. PATENT DOCUMENTS

| | | | |
|---|---|---|---|
| 5,763,689 A | 6/1998 | Boyd et al. | |
| 5,958,757 A | 9/1999 | Steffan et al. | |
| 6,087,137 A | 7/2000 | Blacker et al. | |
| 6,284,865 B1 | 9/2001 | Tam et al. | |
| 6,531,424 B2 | 3/2003 | Ittel et al. | |

FOREIGN PATENT DOCUMENTS

JP 7053429 2/1995

OTHER PUBLICATIONS

Smit, C. et al. Phosphasilenes: Synthesis and Spectroscopic Characterization, Organometallics. 1987, vol. 6, No. 6, pp. 1156-1163.

Gotteland, J. et al. Design and Synthesis of New Hypocholesterolemic Organolsilanes With Antioxidant Properties. Bioorganic & Medicinal Chemistry Letters, 1996, vol. 6, No. 5, pp. 533-538.

Mondello, F.J., Cloning and Expression in *Escherichia coli* of Pseudomonas Strain LB400 Genes Encoding Polycholorinated Biphenyl Degradation, Journal of Bacteriology, Mar. 1989, vol. 171, No. 3, pp. 1725-1732.

Zylstra et al., Toluene Degradation by *Pseudomonas putida* FI: Nucleotide Sequence of the todC12BADE Genes and Their Expression in *Escherichia coli*\*, The Journal of Biological Chemistry, vol. 264, No. 28, Issue of Sep. 5, pp. 14940-14946.

Simon et al., Sequences of genes encoding napthalene dioxygenase in *Pseudomonas putida* strains G7 and NCIB 9816-4, Gene 127 (1993), pp. 31-37.

Whited et al., Oxidation of 2-Methoxynaphthalene by Toluene, Naphthalene and Biphenyl Dioxygenases: Structure and Absolute Stereochemistry of Metabolites, Bioorganic & Medicinal Chemistry, vol. 2, No. 7, pp. 727-734, 1994.

Hudlicky, Natural Product Synthesis via Biocatalysis: An Essay on the Merits of Multidisciplinary Ventures, J. Braz. Chem. Soc., vol. 9, No. 4, pp. 313-318, 1998.

Enzymatic Dihydroxylation of Aromatics in Enantioselective Synthesis: Expanding Asymmetric Methodology, Aldrichimica Acta, vol. 32, No. 2, 1999, pp. 32-72.

Organic Synthesis—An Annual Publication of Satisfactory Methods for the Preparation or Organic Chemicals, vol. 76, 1999, John Wiley & Sons, Inc., pp. 77-83.

*Primary Examiner*—Samuel Bart
(74) *Attorney, Agent, or Firm*—Dinsmore & Shohl LLP

(57) ABSTRACT

The present invention is related to cis-diols and biological methods of producing cis-diols. The present invention further relates to processes for subsequently converting such silane cis-diols to the more stable acetonide derivatives, as well as a process for converting silane cis-diols to the corresponding catechols and the compounds produced thereby. The present invention also provides chemical methods for the conversion of said silane cis-diols and acetonide compounds to epoxy, saturated and otherwise modified derivatives. It is emphasized that this abstract is provided to comply with the rules requiring an abstract which will allow a searcher or other reader to quickly ascertain the subject matter of the technical disclosure. It is submitted with the understanding that is will not be used to interpret or limit the scope or meaning of the claims 37 CFR 1.72(b).

4 Claims, No Drawings

SYNTHESIS OF CIS-DIOLS FROM ARYL SILANES

CROSS REFERENCE TO RELATED APPLICATION

This application claims priority to U.S. Provisional Application No. 60/385,373, filed Jun. 3, 2002 and to U.S. Provisional Application No. 60/435,187 filed Dec. 18, 2002.

BACKGROUND OF THE INVENTION

The present invention relates to dioxygenation of aryl silanes and, more particularly, to processes for converting aryl silanes to a new class of chiral cis-diols by contact with a chemical or biological catalyst such as dioxygenase-producing bacteria in the presence of molecular oxygen ($O_2$) and the chiral cis-diols produced thereby. The present invention further relates to a process for subsequently converting such silane cis-diols to the more stable acetonide derivatives, as well as a process for converting silane cis-diols to the corresponding catechols by treatment with diol dehydrogenase enzyme and the compounds produced thereby. The present invention also provides chemical methods for the conversion of said silane cis-diols and acetonide compounds to epoxy, saturated and otherwise modified derivatives. The chiral intermediates produced by the process of the instant invention represent a novel class of compounds having potential value in the synthesis of fine chemicals, including pharmaceuticals. It is also contemplated that the chiral silicon materials of the present invention may find application in enantioselective separations and optical applications.

The enzymatic dioxygenation of substituted aromatics to cis-diols is known in the art as a means for synthesizing certain chiral molecules from achiral precursors. Several enzymes are known to affect this transformation, including toluene dioxygenase (EC 1.14.12.11), naphthalene dioxygenase (EC 1.14.12.12), and other aromatic oxygenases, which act on or catalyze a wide range of substrates. The following diagram illustrates this catalytic reaction:

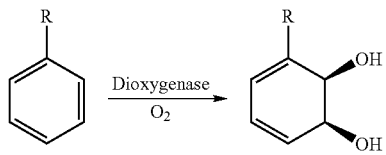

Although the biotransformation of non silicon-containing substituted aromatics to cis-diols by enzymatic dioxygenation is known (e.g., Hudlicky T. et al., (1999) Enzymatic dihydroxylation of aromatics in enantioselective synthesis: expanding asymmetric methodology, *Aldrichimica Acta*, Vol. 32, No. 2, pp. 35–62), there is a need for processes that convert aryl silanes to chiral cis-diols or catechols and for such chiral cis-diols or catechols.

SUMMARY OF THE INVENTION

In accordance with one aspect of the present invention, a method for converting an aryl silane to a corresponding cis-diol is provided. The method comprises providing an aryl silane substrate, wherein the aryl silane has at least one aromatic component and at least one silicon atom, and contacting a dioxygenase enzyme with the aryl silane substrate such that said aryl silane substrate is converted to a corresponding cis-diol. The method may further comprise reacting the cis-diol with 2,2-dimethoxypropane to convert the cis-diol to an acetonide derivative. The method may further comprises contacting a diol dehydrogenase enzyme with the cis-diol to convert the cis-diol to a corresponding catechol.

In accordance with another aspect of the present invention, a compound comprising a cis-diol is provided. The cis-diol has the formula:

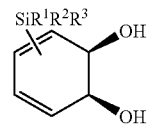

wherein: $R^1$, $R^2$, and $R^3$ are each independently selected from hydrogen, a halogen, an aryl, a linear or branched $C_1$–$C_{18}$ alkyl, a linear or branched $C_2$–$C_{18}$ alkenyl, a linear or branched $C_2$–$C_{18}$ alkynyl, OR, SR, $NR_{2-3}$, or O(CO)R; and R is hydrogen, linear or branched $C_1$–$C_{18}$ alkyl, or $SiR^1R^2R^3$.

In accordance with yet another aspect of the present invention, a compound comprising a cis-diol is provided. The compound has the formula:

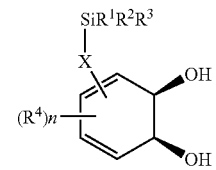

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$ alkyl, $C_2$–$C_{18}$ alkenyl, or $C_2$–$C_{18}$ alkynyl spacer, except when X=$C_2$ alkynyl and $R^1$=$R^2$=$R^3$ then $R^1$=$R^2$=$R^3$ cannot be —$CH_3$.

In accordance with a further aspect of the present invention, a compound comprising a silane cis-diol is provided. The compound has the formula:

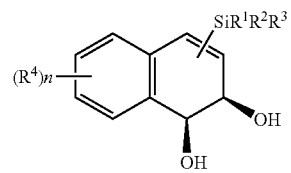

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; and R is hydrogen, linear or branched $C_1$–$C_{18}$ alkyl, or $SiR^1R^2R^3$.

In accordance with the present invention, a compound comprising a silane cis-diol is provided. The compound has the formula:

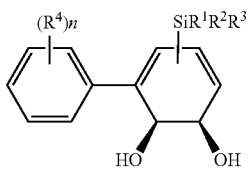

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; and R is hydrogen, linear or branched $C_1$–$C_{18}$ alkyl, or $SiR^1R^2R^3$.

In accordance with a further aspect of the present invention, a compound comprising a silane cis-diol is provided. The compound has the formula:

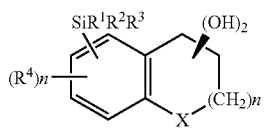

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$alkyl, $C_2$–$C_{18}$ alkenyl, $C_2$–$C_{18}$ alkynyl spacer, S, O or $NR_{1-2}$.

In accordance with another aspect of the present invention, a compound comprising an acetonide is provided. The compound has the formula:

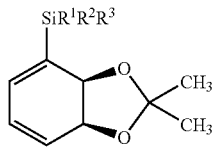

wherein: $R^1$, $R^2$, and $R^3$ are each independently selected from hydrogen, a halogen, an aryl, a linear or branched $C_1$–$C_{18}$ alkyl, a linear or branched $C_2$–$C_{18}$ alkenyl, a linear or branched $C_2$–$C_{18}$ alkynyl, OR, SR, $NR_{2-3}$, or O(CO)R, except when $R^1=R^2=R^3$ then $R^1=R^2=R^3$ cannot be —$CH_3$; and R is hydrogen, linear or branched $C_1$–$C_{18}$ alkyl, or $SiR^1R^2R^3$.

In accordance with yet another aspect of the present invention, a compound comprising an acetonide is provided. The compound has the formula:

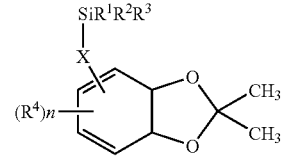

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$ alkyl, $C_2$–$C_{18}$ alkenyl, or $C_2$–$C_{18}$ alkynyl spacer, except when $X=C_2$ alkynyl and $R^1=R^2=R^3$ then $R^1=R^2=R^3$ cannot be —$CH_3$.

In accordance with a further aspect of the present invention, a compound comprising an acetonide is provided. The compound has the formula:

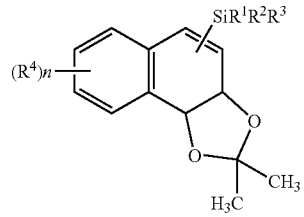

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; and R is hydrogen, linear or branched $C_1$–$C_{18}$ alkyl, or $SiR^1R^2R^3$.

In accordance with another aspect of the present invention, a compound comprising an acetonide is provided. The compound has the formula:

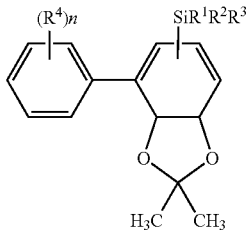

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; and R is hydrogen, linear or branched $C_1$–$C_{18}$ alkyl, or $SiR^1R^2R^3$.

In accordance with yet another aspect of the present invention, a compound comprising an acetonide is provided. The compound has the formula:

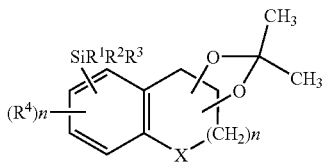

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$alkyl, $C_2$–$C_{18}$ alkenyl, $C_2$–$C_{18}$ alkynyl spacer, S, O or $NR_{1-2}$.

In accordance with a further aspect of the present invention, a compound comprising a catechol is provided. The compound has the formula:

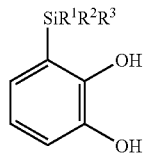

wherein: $R^1$, $R^2$, and $R^3$ are each independently selected from hydrogen, a halogen, an aryl, a linear or branched $C_1$–$C_{18}$ alkyl, a linear or branched $C_2$–$C_{18}$ alkenyl, a linear or branched $C_2$–$C_{18}$ alkynyl, OR, SR, $NR_{2-3}$, or O(CO)R; and R is hydrogen, linear or branched $C_1$–$C_{18}$alkyl, or $SiR^1R^2R^3$.

In accordance with another aspect of the present invention, a compound comprising a catechol is provided. The compound has the formula:

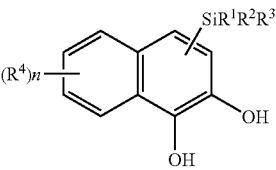

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$alkyl, $C_2$–$C_{18}$ alkenyl, $C_2$–$C_{18}$ alkynyl spacer.

In accordance with a further aspect of the present invention, a compound comprising a catechol is provided. The compound has the formula:

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; and R is hydrogen, linear or branched $C_1$–$C_{18}$ alkyl, or $SiR^1R^2R^3$.

In accordance with another aspect of the present invention, a compound comprising a catechol is provided. The compound has the formula:

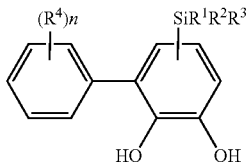

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–5; R is hydrogen, linear or branched $C_1$–$C_{18}$ alkyl, or $SiR^1R^2R^3$.

In accordance with yet another aspect of the present invention, a compound comprising a catechol is provided. The compound has the formula:

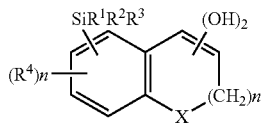

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is a divalent linear or branched $C_1$–$C_{18}$alkyl, $C_2$–$C_{18}$ alkenyl, $C_2$–$C_{18}$ alkynyl spacer, S, O or $NR_{1-2}$.

In accordance with another aspect of the present invention, a compound is provided. The compound comprises:

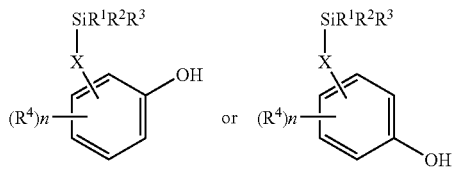

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$alkyl, $C_2$–$C_{18}$ alkenyl, $C_2$–$C_{18}$ alkynyl spacer, except that when X=nothing then $R^1$, $R^2$, and $R^3$ cannot be $R^1=R^2=CH_3$ and $R^3=R^1=R^2=R^3=CH_3$.

In accordance with another aspect of the present invention, a di-O-acyl is provided. The compound has the formula:

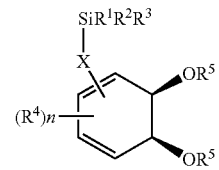

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; $R^5$ is linear or branched $C_1$–$C_{18}$ alkyl, halomethyl, linear or branched $C_2$–$C_{18}$ alkenyl, or linear or branched $C_2$–$C_{18}$ alkynyl; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with a further aspect of the present invention, a silyl ether is provided. The compound has the formula:

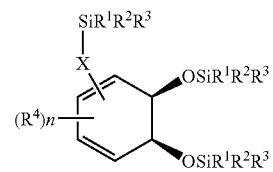

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, or $C_2$–$C_{18}$ alkynyl spacer.

In accordance with another aspect of the present invention, a boronate ester is provided. The compound has the formula:

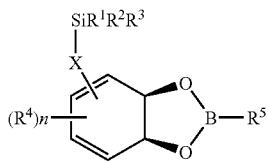

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2\text{-}3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2\text{-}3}$, O(CO)R, $SiR^1R^2R^3$, or a bridging group between two arene or substituted arene moieties; n is 0–3; $R^5$ is aryl, linear or branched $C_1$–$C_{18}$ alkyl, linear or branched $C_2$–$C_{18}$ alkenyl, or linear or branched $C_2$–$C_{18}$ alkynyl; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with another aspect of the present invention, an epoxy is provided. The compound has the formula:

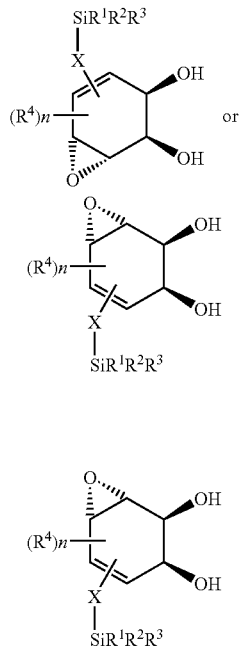

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2\text{-}3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2\text{-}3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with a further aspect of the present invention, an epoxy is provided. The compound has the formula:

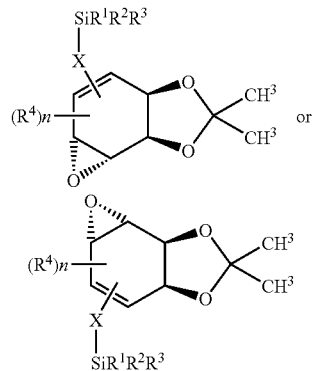

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2\text{-}3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2\text{-}3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer, except when X=nothing then $R^1$, $R^2$, and $R^3$ cannot be $R^1$=$R^2$=$R^3$=$CH_3$.

In accordance with another aspect of the present invention, a partially or fully saturated compound is provided. The compound has the formula:

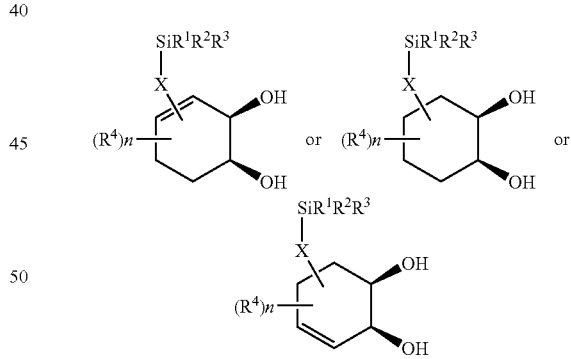

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2\text{-}3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2\text{-}3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with yet another aspect of the present invention, a partially or fully saturated compound is provided. The compound has the formula:

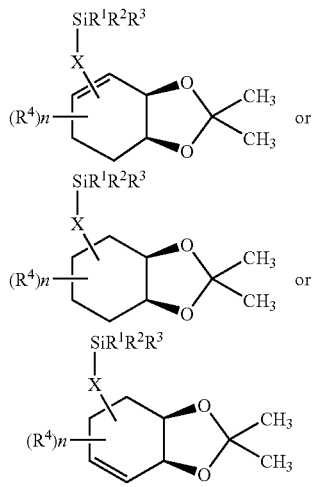

or wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with another aspect of the present invention, a silanol is provided. The compound has the formula:

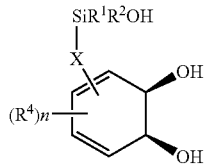

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with yet another aspect of the present invention, a silanol is provided. The compound has the formula:

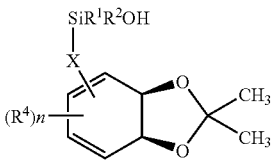

wherein: $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with a further aspect of the present invention, an alkoxy compound is provided. The compound comprises:

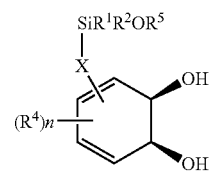

wherein: $R^1$ and $R^2$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; $R^5$ is an aryl, a linear or branched $C_1$–$C_{18}$ alkyl, a linear or branched $C_2$–$C_{18}$ alkenyl, a linear or branched $C_2$–$C_{18}$ alkynyl; n is 0–3; R is hydrogen, linear or branched $C_1$–$C_{18}$ alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

In accordance with another aspect of the present invention, an alkoxy compound is provided. The compound comprises:

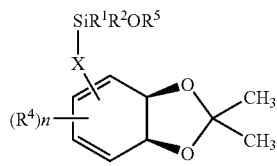

wherein: $R^1$ and $R^2$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties; $R^5$ is an aryl, a linear or branched $C_1$–$C_{18}$ alkyl, a linear or branched $C_2$–$C_{18}$ alkenyl, a linear or branched $C_2$–$C_{18}$ alkynyl; n is 0–3; R is hydrogen, linear or branched $C_1$–$C_{18}$alkyl, or $SiR^1R^2R^3$; and X is nothing, a divalent linear or branched $C_1$–$C_{18}$ alkyl, $C_2$–$C_{18}$ alkenyl, and $C_2$–$C_{18}$ alkynyl spacer.

DETAILED DESCRIPTION OF THE PREFERRED EMBODIMENTS

For purposes of defining and describing embodiments of the present invention, the following terms will be understood as being accorded the definitions presented hereinafter.

As used herein, the term "independently" or the equivalents thereof is employed to described an instance were two or more groups may be the same or different from each other and the occurrence of one group does not impact or influence the occurrence of the other group.

The term "alkyl" refers to a monovalent alkane (hydrocarbon) derived radical containing from 1 to 18 carbon atoms unless otherwise defined. It may be straight or branched. Suitable straight or branched alkyl groups include methyl, ethyl, propyl, isopropyl, butyl, 3-butyl, and t-butyl. Alkyl also includes a straight or branched alkyl group that contains or is interrupted by a cycloalkane portion.

The term "alkenyl" refers to a hydrocarbon radical straight or branched containing from 2 to 18 carbon atoms and at least one carbon to carbon double bond. Preferably one carbon to carbon double bond is present, and up to four non-aromatic (non-resonating) carbon-carbon double bonds may be present. Suitable alkenyl groups include ethenyl, propenyl, and butenyl.

The term "alkynyl" refers to a hydrocarbon radical straight or branched containing from 2 to 18 carbon atoms and at least one carbon to carbon triple bond. Up to three carbon-carbon triple bonds may be present. Suitable alkynyl groups include ethynyl, propynyl, and butynyl.

The term "alkoxy" refers to an alkyl group of indicated carbon atoms attached through an oxygen linkage.

The term "halogen" refers to fluorine, chlorine, bromine, iodine.

The term "halomethyl" referst to a carbon with one or more halogen substituent.

The term "aryl" refers to a substituted aromatic hydrocarbon ring. Suitable aryl groups include single-ring, fused, and biphenyl aromatics.

The term "bridging group" refers to a moiety joining an aromatic and a silicon-containing functionality.

The term "arene" refers to an aromatic compound The term "spacer" refers to a group between an aromatic and a silicon-containing functionality.

The term 'OD' or optical density refers to the optical absorbance of a culture measured at 600 nm.

The term 'TLC' refers to thin layer chromatography.

In accordance with an embodiment of the present invention, processes that are effective in converting aryl silane substrates to silane cis-diols are provided, and silane cis-diol compositions are provided. Such processes include contacting a substrate, e.g., a compound of Formulae I–I'''' as defined below, with a catalyst such as a dioxygenase enzyme, and obtaining the desired cis-diol. The cis-diol may be obtained by recovering the resulting compound of Formulae II–II'''' as defined below. The process may further include isolating and purifying the resulting compound. It is further contemplated that the resulting compound could be used as an intermediate substrate useful in the preparation of other derivatives or end-products.

The present invention provides a method for a biological production of cis-diols from a fermentable silicon substrate by a microorganism grown with a suitable carbon source. Examples of suitable carbon sources include, but are not limited to, glucose, fructose, sucrose or glycerol and mixtures thereof. The method comprises providing a dioxygenase enzyme, contacting the dioxygenase enzyme with an aryl silane substrate, and obtaining a cis-diol from the growth media. The dioxygenase enzyme may be provided in any suitable manner. For example, the enzyme may be present in whole cells or cell-free. The term "whole cells" refers to a intact microorganism that expressed the desired enzymatic catalyst. The microorganism can be a wild type microorganism that is known to express or produce the desired enzymatic catalyst, e.g., P. putida. The term cell free refers to an extract or solution of the desired enzyme catalyst. The enzyme may be provided in a wild-type microorganism or it may be provided in a genetically altered organism harboring a gene encoding a dioxygenase enzyme. In addition to an appropriate aryl silane substrate, the fermentation media generally contains suitable carbon sources (hexoses such as glucose, pentoses such as fructose, etc.), minerals, salts, cofactors, buffers and other components, known to those skilled in the art, suitable for the growth of the cultures and promotion of the enzymatic pathway necessary for cis-diol production.

Generally, cells are grown at appropriate temperatures and in appropriate media. Suitable growth media in the present invention are minimal mineral salts media to facilitate the subsequent extraction of the products. Suitable pH ranges for the fermentation are between pH 5.0 to pH 9.0 where pH 6.8 to pH 8.0 is preferred as the initial condition.

In accordance with a further embodiment of the present invention, aryl silanes are dioxygenated to their corresponding cis-diols. A corresponding cis-diol refers to the conversion of an aryl silane substrate by the attachment of two hydroxyl groups to adjacent carbons in a cis configuration with respect to one another by the catalytic action of a dioxygenase upon the substrate. The conversion of aryl silanes to the corresponding cis-dol derivatives results in the loss of aromaticity of the ring that underwent dioxygenation. For purposes of defining and describing the present invention, "aryl silane" shall be understood as referring to a compound containing at least one aromatic ring and at least one silicon atom. In one aspect the aromatic components include substituted single ring, fused or biphenyl aromatics. Exemplary aromatic components include, but are not limited to, phenyl, naphthyl or biphenyl derivatives having a silicon-containing group. Other exemplary aromatics include, but are not limited to, those containing additional fused heterocyclic or carbocyclic rings, e.g, silicon substituted indoles and/or indenes. The silicon atom can be contained in a silicon containing substituent, e.g. the silicon atom is either directly attached to the aromatic ring or attached through a spacer element. Such aryl silanes are available through well known synthetic methods (e.g., Murata, M. et al. (2002) Rhodium(I)-Catalyzed Silylation of Aryl Halides with Triethoxysilane: Practical Synthetic Route to Aryltriethoxysilanes. *Org. Letters,* Vol. 4, No. 11, pp 1843–1845). Further contemplated by the present invention is the subsequent conversion of silane cis-diols to the corresponding catechols. A corresponding catechol refers to the conversion of a cis-diol substrate by the dehydrogenation of the substrate by the catalytic action of a diol dehydrogenase upon the substrate wherein the aromaticity is restored and results in the formation of a catechol derivative. A summation of these catalytic reactions is illustrated below:

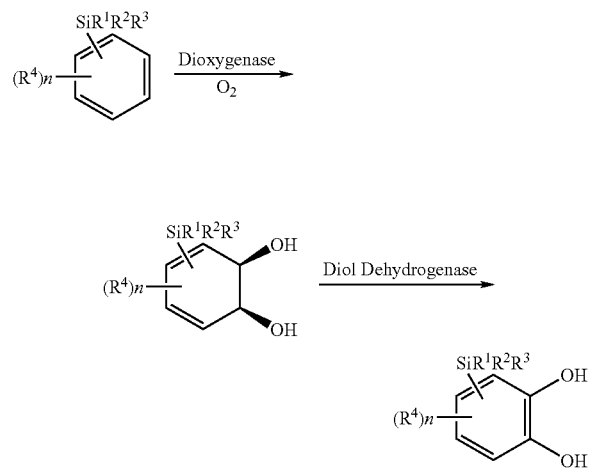

The chemistry of silicon renders the intermediate silane cis-diols of the instant invention unique relative to the substituents described by the prior art, which comprise carbon, halogen, or heteroatom functionalities. For example, the scientific literature records many examples of reactions that are particular to silicon and not the corresponding carbon analogs. These reactions include hydrosilylation of alkenes and ketones, the addition of electrophiles to vinyl and allyl silanes, and palladium catalyzed cross-coupling of vinyl silanes with aryl halides (Brook, M. A., Silicon in Organic, Organometallic and Polymer Chemistry (2000), Wiley). The silane cis-diols may be used: as chiral intermediates, for synthesizing polymers, as chiral separators, to form optically active materials, to act as carbohydrate analogs, and as intermediates in natural products synthesis.

In accordance with an embodiment of the present invention, a process is provided for conversion of a compound of the Formula (I):

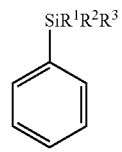

Formula (I)

into a compound of the Formula (II):

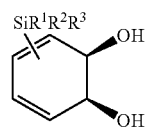

Formula (II)

using a dioxygenase enzyme;

wherein:

$R^1$, $R^2$, and $R^3$ are each independently selected from hydrogen, a halogen, an aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R; and R is hydrogen, linear or branched $C_1$–$C_{18}$ alkyl, or $SiR^1R^2R^3$.

The present invention is not limited, however, to these particular substituents. It is therefore contemplated that the compounds of Formulas (I) and (II) can include any substituent containing at least one silicon atom and the silicon atom need not be directly bonded to the aromatic ring, which itself may be multiply substituted with a range of functionality, including additional silicon-containing groups. For example, the silicon may be included as part of a chain of between 1 and 18 carbons, including branched and unsaturated carbon chains with both double and triple bonding attached to an arene moiety substituted with a halogen or other group. Furthermore, the introduced hydroxyl groups need not be directly adjacent to the group containing silicon. For example, such hydroxyl groups could one or more carbons removed from the group containing silicon. The prior art records instances where the introduction of additional functionality such as an iodo (I) group to a monosubstituted arene alters the regioselectivity of dihydroxylation with respect to the initial functionality (see, for example, EP 717729B1 or U.S. Pat. No. 5,763,689, both to Boyd et al.).

In one aspect of the present invention, $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR; and R is hydrogen, methyl, or ethyl. In another aspect of the present invention, $R^1$, $R^2$, and $R^3$ are each independently selected from hydrogen, methyl, chloromethyl, or vinyl.

Examples of suitable aryl silane substrates and the corresponding cis-diols are shown below in Scheme 1.

Scheme 1.
Conversion of aryl silanes to cis-diol products

| Aryl silane substrate | | cis-diol product | |
|---|---|---|---|
| 1a | 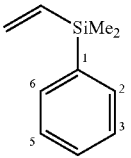 Dimethylphenylvinylsilane | 2a | 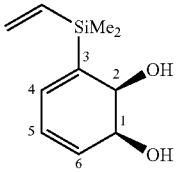 (1S,2S)-3-(dimethylvinylsilyl)cyclohexa-3,5-diene-1,2-diol |
| 1b | 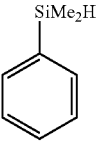 Dimethylphenylsilane | 2b | 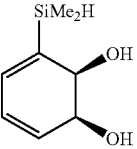 (1S,2S)-1-(dimethylsilyl)cyclohexa-3,5-diene-1,2-diol |
| 1c | 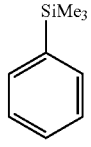 Phenyltrimethylsilane | 2c | 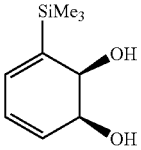 (1S,2S)-3-(trimethylsilyl)cyclohexa-3,5-diene-1,2-diol |
| 1d | 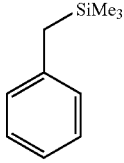 Benzyltrimethylsilane | 2d | 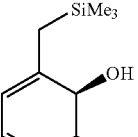 (1S,2R)-3-(trimethylsilylmethyl)cyclohexa-3,5-diene-1,2-diol |
| 1e | 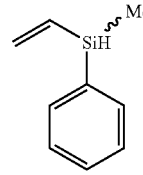 (R,S)-methylphenylvinylsilane | 2e | 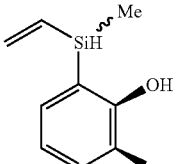 (1S,2S)-1-[(R,S)-methylvinylsilyl]cyclohexa-3,5-diene-1,2-diol |

-continued

Scheme 1.
Conversion of aryl silanes to cis-diol products

| Aryl silane substrate | cis-diol product |
|---|---|
| 1f 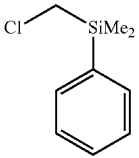 (Chloromethyl)dimethylphenylsilane | 2f 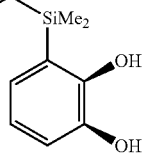 (1S,2S)-3-[(chloromethyl)dimethylsilyl]cyclohexa-3,5-diene-1,2-diol |

In accordance with another aspect of the present invention, a process is provided for conversion of a compound of the Formula (I'):

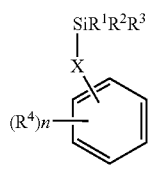

Formula (I')

into a compound of the Formula (II'):

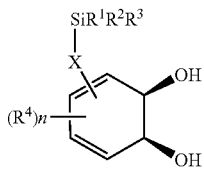

Formula (II')

using a dioxygenase enzyme;
wherein:
$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;
$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;
n is 0–3;
R is hydrogen, linear or branched $C_1$–$C_{18}$ alkyl, or $SiR^1R^2R^3$;
X is a divalent linear or branched $C_1$–$C_{18}$ alkyl, $C_2$–$C_{18}$ alkenyl, or $C_2$–$C_{18}$ alkynyl spacer.
However, when X=$C_2$ alkynyl and $R^1$=$R^2$=$R^3$ then $R^1$=$R^2$=$R^3$ cannot be —$CH_3$.

This aspect of the present invention is also intended to apply where compounds of formulas (I') and (II') occur in the context of a polymer linked through one of more of the functionalities R and $R^1$–$R^4$. For example, the arene units of a diblock copolymer consisting of polydimethylsiloxane (PDMS) and polyphenylmethylsiloxane (PPMS) could be wholly or partially converted to the corresponding cis-diols.

In one embodiment, $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR; $R^4$ is selected from hydrogen, halogen, a linear or branched $C_1$–$C_5$ alkyl, a linear or branched $C_2$–$C_5$ alkenyl, a linear or branched $C_2$–$C_5$ alkynyl, CN, $NO_2$, OR or $SiR^1R^2$, $R^3$; R is hydrogen, methyl, or ethyl; and X is either a divalent linear or branched $C_1$–$C_5$ alkyl, $C_2$–$C_5$ alkenyl, or $C_2$–$C_5$ alkynyl spacer. In yet another embodiment, $R^1$, $R^2$, and $R^3$ are each independently selected from hydrogen, methyl, chloromethyl, or vinyl and $R^4$ selected from hydrogen, halogen, a linear or branched $C_1$–$C_3$ alkyl, a linear or branched $C_2$–$C_3$ alkenyl, a linear or branched $C_2$–$C_3$ alkynyl, CN, $NO_2$, OR or $SiR^1R^2R^3$.

In accordance with still another aspect of the present invention, a process is provided for conversion of a compound of the Formula (I"):

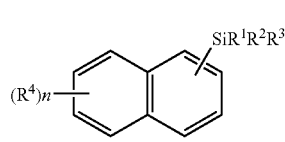

Formula (I")

into a compound of the Formula (II"):

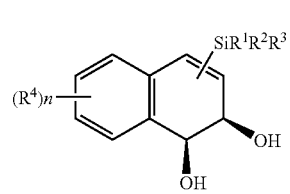

Formula (II")

using a dioxygenase enzyme;
wherein:
$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;

$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–5; and

R is hydrogen, linear or branched $C_1$–$C_{18}$ alkyl, or $SiR^1R^2R^3$.

In one embodiment, $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR; $R^4$ is selected from hydrogen, halogen, a linear or branched $C_1$–$C_5$ alkyl, a linear or branched $C_2$–$C_5$alkenyl, a linear or branched $C_2$–$C_5$ alkynyl, CN, $NO_2$, OR or $SiR^1R^2R^3$; and R is hydrogen, methyl, or ethyl. In yet another embodiment, $R^1$, $R^2$, and $R^3$ are each independently selected from hydrogen, methyl, chloromethyl, or vinyl and $R^4$ is selected from hydrogen, halogen, a linear or branched $C_1$–$C_3$ alkyl, a linear or branched $C_2$–$C_3$ alkenyl, a linear or branched $C_2$–$C_3$ alkynyl, CN, $NO_2$, OR or $SiR^1R^2R^3$.

In accordance with still another aspect of the present invention, a process is provided for conversion of a compound of the Formula (I'''):

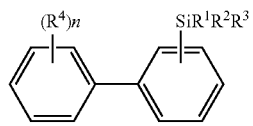

Formula (I''')

into a compound of the Formula (II'''):

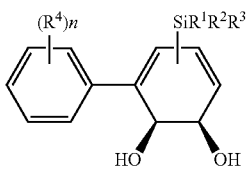

Formula (II''')

using a dioxygenase enzyme;
wherein:
$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;

$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–5; and

R is hydrogen, linear or branched $C_1$–$C_{18}$ alkyl, or $SiR^1R^2R^3$.

In one embodiment, $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR; $R^4$ is selected from hydrogen, halogen, a linear or branched $C_1$–$C_5$ alkyl, a linear or branched $C_2$–$C_5$ alkenyl, a linear or branched $C_2$–$C_5$ alkynyl, CN, $NO_2$, OR or $SiR^1R^2R^3$; and R is hydrogen, methyl, or ethyl. In yet another embodiment, $R^1$, $R^2$, and $R^3$ are each independently selected from hydrogen, methyl, chloromethyl, or vinyl and $R^4$ is selected from hydrogen, halogen, a linear or branched $C_1$–$C_3$ alkyl, a linear or branched $C_2$–$C_3$ alkenyl, a linear or branched $C_2$–$C_3$ alkynyl, CN, $NO_2$, OR or $SiR^1R^2R^3$.

In accordance with still another aspect of the present invention, a process is provided for conversion of a compound of the Formula (I''''):

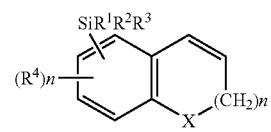

Formula (I'''')

into a compound of the Formula (II''''):

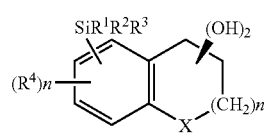

Formula (II'''')

using a dioxygenase enzyme;
wherein:
$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;

$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–3;

R is hydrogen, linear or branched $C_1$–$C_{18}$ alkyl, or $SiR^1R^2R^3$; and

X is a divalent linear or branched $C_1$–$C_{18}$ alkyl, $C_2$–$C_{18}$ alkenyl, $C_2$–$C_{18}$ alkynyl spacer, S, O or $NR_{1-2}$.

The two hydroxyl group substituents are attached to adjacent carbons and are in a cis-configuration with respect to one another.

In one embodiment, $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR; $R^4$ is selected from hydrogen, halogen, a linear or branched $C_1$–$C_5$ alkyl, a linear or branched $C_2$–$C_5$ alkenyl, a linear or branched $C_2$–$C_5$ alkynyl, CN, $NO_2$, OR or $SiR^1R^2R^3$; R is hydrogen, methyl, or ethyl; and X is either a divalent linear or branched $C_1$–$C_5$ alkyl, $C_2$–$C_5$ alkenyl, or $C_2$–$C_5$ alkynyl spacer. In yet another embodiment, $R^1$, $R^2$, and $R^3$ are each independently selected from hydrogen, methyl, chloromethyl, or vinyl and $R^4$ is selected from hydrogen, halogen, a linear or branched $C_1-C_3$ alkyl, a linear or branched $C_2-C_3$ alkenyl, a linear or branched $C_2-C_3$ alkynyl, CN, $NO_2$, OR or $SiR^1R^2R^3$.

It will be understood by those having skill in the art that the compounds of Formula (II)-(II'''') comprise a novel class of chiral cis-diols containing silicon. It will be further understood that the present invention encompasses the compounds of Formula (II)-(II''''). The cis-diol may be present in an enantiomeric excess of between about 10 to about 100 percent. Alternatively, the cis-diol may be present in an enantiomeric excess of between about 70 to about 100 percent, or greater than about 95 percent, or greater than about 98 percent. It will be further understood that the methods of the present invention may comprise providing a plurality of aryl silane substrates. The plurality of aryl silane substrates comprise the same aryl silane, or the plurality of aryl silane substrates comprise different aryl silanes.

The dioxygenase enzyme can be any aromatic dioxygenase enzyme, recombinant or otherwise; for example toluene dioxygenase (EC 1.14.12.11), naphthalene dioxygenase (EC 1.14.12.12), biphenyl dioxygenase (EC 1.14.12.18). It is contemplated that the dioxygenase enzyme that contacts the substrate can be in any form that effectively transforms a compound of Formula (I)–(I'''') into a compound of Formula (II)–(II''''), respectively. For example, the aromatic dioxygenase enzyme can be in the form of a cell-free extract, a synthetic form, disintegrated cells, or whole cells. For example, the dioxygenase enzyme is present in whole cells in various strains of *E. coli*, which express the toluene dioxygenase enzyme from *P. putida*. The construction of host cells expressing toluene dioxygenase JM109 (SEQ ID No. 1), e.g., containing a plasmid that expresses toluene dioxygenase is described in Zylstra, G. J. and Gibson, D. T., *Toluene degradation by Pseudomonas putida F1, Nucleotide sequence of the todC1C2BADE genes and their expression in Escherichia coli*, J. Biol. Chem. 264: 14940–14946 (1989), which is incorporated by reference herein. The nucleotide sequence of *P. putida* toluene dioxygenase and cis-toluene dihydrodiol dehydrogenase (todC1C2BAD) is given below (SEQ ID No. 1) and has an accession number of J04996.

```
   1 gaattcgttc ggcggtgcct tgtctctggc ctttgctatc cgatttccgc atcgggttcg
  61 ccgcctggtg ctgatgggtg ccgttggcgt gagcttcgag ctcacggatg gactggatgc
 121 agtttggggt tatgagccgt ccgtgccgaa catgcgcaag gtcatggact acttcgccta
 181 cgaccgaagt ctcgtttccg acgaactggc ggaactgcgc tacaaggcga gcacccggcc
 241 cggttttcag gaggccttcg cttccatgtt ccctgctccg cggcagcgct gggtagatgc
 301 gctggccagt tccgatcagg acatccggga catccggcat gaaacgctga tcctgcatgg
 361 ccgcgacgat cgcgtgattc ccctcgaaac ctcgttgcgg ctgaaccagc tgatcgaacc
 421 ctcccagtta catgtctttg gcaggtgtgg ccattgggtg cagatcgagc aaaaccgggg
 481 ctttatccgc ttggtcaacg attttcttgc cgcggaggac tgatcgcaaa acgggaatg
 541 accatccgtt ctgaaagcac gtcatcggca attgcctgcc aagtacccgc catccactac
 601 cttgaaaagt gagaagacaa tgaatcagac cgacacatca cctatcaggc tgcgcaggag
 661 ctggaacacc agcgagatag aagcgctctt tgacgagcat gccggacgta tcgatccgcg
 721 catttatacc gatgaggatc tgtaccaact cgaactggag cgtgtcttcg cccggtcctg
 781 gctgctgttg gggcatgaaa cccagattcg caagccgggc gattacatca cgacctacat
 841 gggtgaagac cctgtcgtgg tcgtccggca gaaagacgcc agcattgccg tgttcctgaa
 901 ccagtgccgc caccgtggca tgcgcatctg ccgcgcggat gccggaaacg cgaaggcgtt
 961 cacttgcagc taccacgggt gggcttacga caccgccggc aatcttgtca atgtgcctta
1021 cgaggccgaa tccttcgcgt gcctgaacaa gaaggaatgg agcccgctga aggcccgggt
1081 agaaacctac aagggcctga ttttcgccaa ctgggatgag aacgctgtag acctcgacac
1141 gtatctgggc gaggcgaagt tctacatgga ccacatgctc gaccgcaccg aggccggcac
1201 cgaagcgatc ccgggcgtgc agaagtgggt cattccctgt aactggaaat tcgccgcaga
1261 gcagttttgc agcgacatgt accatgccgg gacgacctcg catctgtctg gcatcctggc
1321 aggcctgcca gaagaccttg aaatggccga ccttgctccg ccgacagttg gcaagcagta
1381 ccgtgcgtca tggggcggac atggaagtgg cttctatgtc ggcgacccca atctgatgct
1441 tgccatcatg gggccaaagg tcaccagcta ctggaccgaa ggccccgcgt cggaaaaggc
1501 ggccgaacgt ctgggtagcg tggagcgcgg ctcgaaactc atggtcgagc acatgaccgt
```

-continued

```
1561  cttccccacg tgttccttcc tcccaggtat caatacggtc cggacatggc atccgcgcgg
1621  gccgaacgag gtcgaggtat gggcgtttac ggtggtcgat gctgatgctc ctgacgatat
1681  caaggaagag ttccggcgcc agacgctgcg caccttctct gccggtggcg tgttcgagca
1741  ggacgacggg gagaactggg tcgagatcca gcacatcctg cgaggccaca ggcgcggag
1801  ccgcccttc aatgccgaga tgagcatgga ccagaccgtc gacaacgacc cggtttaccc
1861  cgggcggatc agcaacaacg tctacagcga ggaagctgcc cgcgggctct atgcccattg
1921  gctgcggatg atgacatccc ccgactggga cgcgctgaag gcgacacgct gaatccagag
1981  acagcttgcg ccacgcagtg gcgccggcca gaggccgcat ttgacttcga cccaggttgg
2041  atgcggtgga ccttgtccat ttgaaatcta caaggaacga ccatgattga ttcagccaac
2101  agagccgacg tctttctccg caagccggca cccgtagcgc cgaactgca gcacgaagtc
2161  gagcagttct actattggga ggccaagctt ctcaacgatc gccgcttcga ggagtggttc
2221  gcgctgctcg cggaagacat tcactacttc atgcccattc gcaccacgcg gatcatgcgg
2281  gactcgcgcc ttgaatactc aggctcccga gagtacgcgc acttcgatga cgacgccacg
2341  atgatgaagg gacgcttgcg caagatcacg tccgacgtga gctggtccga gaaccccgca
2401  tcgcggaccc ggcatctcgt gagcaacgtg atgatcgtcg gcgcagaggc agaaggggag
2461  tacgaaatct caagcgcctt cattgtgtac cgcaatcgtc tggagcggca gctcgacatc
2521  tttgccggtg agcgtcgcga tacgttgcgc cgtaacacga gcgaggccgg gttcgagatc
2581  gtcaatcgga ccatcctgat cgaccagagc accatcctgg ccaataacct cagtttcttc
2641  ttctaggtga tgtcatgact tggacataca tattgcggca gggtgacctg ccacccggtg
2701  agatgcagcg ctacgaaggc ggcccggaac ctgtgatggt ctgcaacgtc gatggcgagt
2761  tcttcgcggt gcaggatacc tgcacgcatg gggactgggc gttgtcggat ggttacctgg
2821  acggtgatat tgtcgaatgc acgttgcatt tcggcaagtt ctgcgtgcgg accgggaagg
2881  tgaaggcgct gcctgcttgc aaacctatca aggtattccc aatcaaggtc gaaggcgatg
2941  aagtgcacgt cgatctcgac aacggggagt tgaagtgatg gctacccatg tggcgatcat
3001  cggcaatggc gtgggtggct tcacgaccgc gcaggcccta cgtgccgagg gcttcgaggg
3061  gagaatctcg ctgattgggg acgaaccgca tctcccctat gaccgaccat ccttgtccaa
3121  ggcggttctc gacggcagcc ttgagcggcc gcccatactg gccgaggccg attggtacgg
3181  cgaggcccgc atcgacatgc tgaccggccc ggaagtcact gcccttgatg tgcagacaag
3241  gacgatcagt ctggatgatg gcaccacgct ctctgcggac gccatcgtca tcgcgacggg
3301  cagtcgagcg cggacgatgg cgttgcccgg cagccaactg cccggcgtcg taacgctgcg
3361  cacctacggt gacgtgcagg tattgcgcga tagttggact tccgcgacgc ggctgctgat
3421  tgtgggtggc ggattgatcg gctgcgaggt cgcgacgacg gcgcgcaagc tcggcctgtc
3481  ggtcacgatc ctggaggcag gtgatgaact gctggtccga gtacttgggc ggcgtatcgg
3541  tgcctggctg cgcggcctgc tgacagaact tggtgtgcag gtcgagttgg aacgggtgt
3601  cgtaggtttt tctggtgagg gccagctcga acaagtcatg gccagcgatg ggcgcagctt
3661  cgtagccgat agcgcactca tttgcgtcgg cgcggagccc gcggatcaac ttgcgcgtca
3721  agcgggcttg gcatgtgacc gcggcgtcat tgtcgatcac tgcggtgcga gcttgccaa
3781  aggcgtattc gccgtcggag atgtggccag ttggccgctg cgcgccggcg gccggcgttc
3841  gctcgaaacc tatatgaacg cgcagcgcca agccgccgcg gtggctgcgg ccattctggg
3901  gaaaaacgta tcggcaccgc aactgcccgt gtcctggacg gagatcgctg ggcatcgcat
```

-continued

```
3961  gcagatggcg ggcgatatcg aaggacctgg tgatttcgtc tcgcgcggca tgcccggtag
4021  tggcgctgcc ctgttgttcc gcctgcagga gcgaaggatt caggcggtcg tcgcggtcga
4081  tgcaccccgt gacttcgcgc ttgcaacccg attggtagaa gcccgcgcgg caatcgagcc
4141  agcacggctg gcagatcttt caaacagtat gcgcgatttt gttcgtgcga atgaaggaga
4201  cctaacgtga gacttgaagg cgaagtggcc ttggtgacag gcggtggcgc aggcctgggc
4261  agagcgatcg tggatcgtta tgtcgcggaa ggtgcgcgtg tcgcggtgct ggataaatcc
4321  gcggcaggcc tggaagcgct caggaaactc catggcgatg caatcgtggg cgtggagggg
4381  gatgttcgct cgctcgacag ccatcgtgag gctgtggccc gctgcgtcga agcgttcggc
4441  aagctggact gcctggttgg caatgctggc gtttgggact acctgaccca actggtggat
4501  attcccgacg acctcatatc ggaggcattc gaggaaatgt cgaggtcaa  tgtcaagggc
4561  tacatcctgg cggcaaaggc tgcgctacct gcgctttatc agagcaaagg cagcgcgata
4621  ttcactgtgt cgaatgccga tttctacccg ggcggtggcg gtgttctgta tacagctggc
4681  aaacatgccg tgattggatt gatcaagcag ctcgcgcacg aatggggcc  gcgtatccgc
4741  gtcaacggca tcgccccgg  tggcattttg gggagcgatc tgcgcgggct gaagagcctt
4801  gatttacaag acaagagcat ttcgaccttt ccattggacg acatgctgaa atccgttctt
4861  ccgaccgggc gggccgccac tgccgaggaa tacgccggcg cctatgtctt cttcgcgacg
4921  cgcggcgaca cggttccgct caccggtagc gtgttgaact tcgatggcgg catgggcgtg
4981  cgtggcttgt tcgaagccag cctaggcgca cagctcgaca agcacttcgg ttga
```

Additionally, the deduced amino acid sequences of *P. putida* toluene dioxygenase (iron-sulfur protein, ferredoxin, reductase) are given below:

Iron-Sulfur Protein Large Subunit (todC1) (SEQ ID No. 2)
Start: 620 Stop: 197
translation=

"MNQTDTSPIRLRRSWNTSEIEALFDEHAGRIDPRIYTDEDLYQLELERV
FARSWLLLGHETQIRKPGDYITTYMGEDPVVVVRQKDASIAVFLNQCRHR
GMRICRADAGNAKAFTCSYHGWAYDTAGNLVNVPYEAESFACLNKKEWSP
LKARVETYKGLIFANWDENAVDLDTYLGEAKFYMDHMLDRTEAGTEAIPG
VQKWVIPCNWKFAAEQFCSDMYHAGTTSHLSGILAGLPEDLEMADLAPPT
VGKQYRASWGGHGSGFYVGDPNLMLAIMGPKVTSYWTEGPASEKAAERLG
SVERGSKLMVEHMTVFPTCSFLPGINTVRTWHPRGPNEVEVWAFTVVDAD
APDDIKEEFRRQTLRTFSAGGVFEQDDGENWVEIQHILRGHKARSRPFNA
EMSMDQTVDNDPVYPGRISNNVYSEEAARGLYAHWLRMMTSPDWDALKAT
R"

Iron-Sulfur Protein Small Subunit (todC2) (SEQ ID No. 3)
Start: 2083 Stop: 2646
translation=

"MIDSANRADVFLRKPAPVAPELQHEVEQFYYWEAKLLNDRRFEEWFALL
AEDIHYFMPIRTTRIMRDSRLEYSGSREYAHFDDDATMMKGRLRKITSDV
SWSENPASRTRHLVSNVMIVGAEAEGEYEISSAFIVYRNRLERQLDIFAG
ERRDTLRRNTSEAGFEIVNRTILIDQSTILANNLSFFF"

Ferredoxin (todB) (SEQ ID No. 4)
Start: 2655 Stop: 2978
translation=

"MTWTYILRQGDLPPGEMQRYEGGPEPVMVCNVDGEFFAVQDTCTHGDWA
LSDGYLDGDIVECTLHFGKFCVRTGKVKALPACKPIKVFPIKVEGDEVHV
DLDNGELK"

Start: 2978 Stop: 4210
translation=

"MATHVAIIGNGVGGFTTAQALRAEGFEGRISLIGDEPHLPYDRPSLSKA
VLDGSLERPPILAEADWYGEARIDMLTGPEVTALDVQTRTISLDDGTTLS
ADAIVIATGSRARTMALPGSQLPGVVTLRTYGDVQVLRDSWTSATRLLIV
GGGLIGCEVTARKLGLSVTILEAGDELLVRVLGRRIGAWLRGLLTELGVQ
VELGTGVVGFSGEGQLEQVMASDGRSFVADSALICVGAEPADQLARQAGL
ACDRGVIVDHCGATLAKGVFAVGDVASWPLRAGGRRSLETYMNAQRQAAA
VAAAILGKNVSAPQLPVSWTEIAGHRMQMAGDIEGPGDFVSRGMPGSGAA
LLFRLQERRIQAVVAVDAPRDFALATRLVEARAAIEPARLADLSNSMRDF
VRANEGDLT"

Cis-Toluene Dihydrodiol Dehydrogenase (todD, gtg Start Codon) (SEQ ID No. 6)
Start: 4207 Stop: 5034
translation=

"MRLEGEVALVTGGGAGLGRAIVDRYVAEGARVAVLDKSAAGLEALRKLH

GDAIVGVEGDVRSLDSHREAVARCVEAFGKLDCLVGNAGVWDYLTQLVDI

PDDLISEAFEEMFEVNVKGYILAAKAALPALYQSKGSAIFTVSNAGFYPG

GGGVLYTAGKHAVIGLIKQLAHEWGPRIRVNGIAPGGILGSDLRGLKSLD

LQDKSISTFPLDDMLKSVLPTGRAATAEEYAGAYVFFATRGDTVPLTGSV

LNFDGGMGVRGLFEASLGAQLDKHFG"

In addition, the construction of host cells expressing naphthalene dioxygenase and biphenyl dioxygenase are described in Simon, M., et al Gene, 127:31–37 (1993); Mondello, F., J. Bacteriology, 171(3):1725–1732 (1989). U.S. Pat. No. 5,173,425 teaches a method for overexpressing a dioxygenase, and it is incorporated by reference herein.

The following dioxygenase-containing organisms can be contacted with the substrates, used to oxidize aryl silanes via enzymatic dioxygenation to their corresponding cis-diols (Whited, G. M. et al. (1994) Oxidation of 2-Methoxynaphthalene by Toluene, Naphthalene and Biphenyl Dioxygenases: Structure and Absolute Stereochemistry of Metabolites. *Bioorganic & Medicinal Chemistry*, Vol. 2, No. 7, pp. 727–734):

| Strain | Phenotype |
|---|---|
| E. coli JM109(pDTG601) | JM109 containing the structural genes for toluene dioxygenase (todC1C2BA) from *Pseudomonas putida* F1 in pKK223-3; dioxygenase is inducible by isopropyl-β-D-thiogalactoside (IPTG); ampicillin and carbenicillen resistant (Amp). |
| E. coli JM109(pDTG602) | JM109 containing the structural genes for toluene dioxygenase and (+)-cis-(1S, 2R)-dihydroxy-3-methylcyclohexa-3,5-diene dehydrogenase (todC1C2BAD) from *Pseudomonas putida* F1 in pKK223-3; dioxygenase is inducible by isopropyl-β-D-thiogalactoside (IPTG); ampicillin and carbenicillen resistant (Amp). |
| Ralstonia eutropha A5 | Wild strain containing polychlorinated biphenyl (PCB) catabolic genes |
| Sphingomonas yanoikuyae B8/36 | Mutant strain containing PCB/biphenyl catabolic genes in which dihydrodiol dehydrogenase (bphB) has been inactivated |
| E. coil C534(ProR/Sac) | C534 containing the structural genes for naphthalene dioxygenase from PpG7 (nahAaAbAcAd) in pAC1; dioxygenase is expressed constitutively (Lambda $P_L$ promoter); Amp. |

The process of this aspect of the present invention can be viewed as a biological production process wherein the compounds of Formulas (I)–(I'''') (a group of aryl silanes) are converted into compounds of Formulas (II)–(II''''), respectively, (a novel class of silane cis-diols) using a dioxygenase enzyme. It should be recognized that the absolute stereochemistry of the cis-diol products can vary according to the dioxygenase used (*Aldrichimica Acta*, Vol. 32, No. 2, pp. 35–62). The process may be carried out in a liquid medium, more specifically, a buffered aqueous medium. Suitable buffers can be inorganic or organic and are typically those that control the pH of the medium in the range of between about 6 and about 8. For example, the buffer may be an inorganic, alkali metal phosphate buffer such as a 100 mM phosphate buffer. The pH of the process may be maintained at a pH of about 6.8 by intermittent feeding of an inorganic base, which may be an alkali metal hydroxide such as dilute aqueous sodium or potassium hydroxide.

A co-substrate that provides for NADH recycle may optionally be added to the liquid medium. Typically, this co-substrate is a sugar or other carbon source (e.g. glycerol), which provides an economical energy source for the enzyme-producing microorganisms. Other optional co-substrates include a-ketoacids and their alkali metal salts (e.g., pyruvic acid and sodium pyruvate) and alcohols (e.g., ethanol and isopropanol).

The process involves oxidation of the compounds of Formulas (I)–(I'''') and the source of oxygen may be molecular oxygen ($O_2$). Therefore, during the process oxygen may be continuously introduced through the liquid medium. For example, the oxygen may be in the form of air. The process may be performed at a temperature from about 25° C. to about 50° C. or between about 30° C. and about 40° C. It will be understood that the cells of the present invention should be fed under conditions that allow the cells to sufficiently metabolize the food source and to optimize the production of the cis-diols.

When the process has proceeded for a suitable period it may be terminated by any appropriate means, for example by centrifugation or filtration and/or by cooling the broth to a temperature of less than about 5° C. The supernatant or product of Formulas (II)–(II'''') may be isolated by any convenient means, for example by solvent extraction, typically using a halocarbon solvent (e.g., $CH_2Cl_2$), an aromatic solvent (e.g., toluene) or an ester (e.g., ethyl acetate) following saturation with sodium chloride. The organic extract can then be dried over sodium sulfate, filtered and dried under vacuum.

In accordance with the present invention, the cis-diol-containing media can then be purified or further isolated to provide the cis-diol composition of the present invention. The inventors contemplate "isolated" as being greater than 90% [pure]. Suitable methods of purification include, but are not limited to biphasic extraction (e.g., aqueous/organic phase extraction), recrystallization from solvents and solvent mixtures known to those of skill in the art, ion exchange such as through a column containing DOWEX® resin, elution chromatography and combinations thereof. Methods of elution chromatography include, but are not limited to preparative thin-layer chromatography, conventional silica gel chromatography, and high performance liquid chromatography. Purification of the cis-diol-containing compositions by any of the above mentioned means may optionally separate the residue into various fractions, each of which may function alone or in combination with any other fraction or fractions as the cis-diols of the present invention.

According to the next aspect of the present invention there is provided a process for the chemical conversion of the cis-diols into more stable acetonide derivatives. In accordance with one embodiment of the present invention, a compound of Formula (II) is converted into the more stable acetonide derivatives of the compound of Formula (III):

Formula (III)

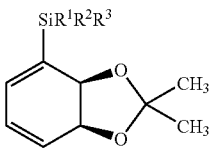

in which $R^1$, $R^2$, and $R^3$ are as hereinbefore defined, by reaction of the compound of Formula (II) with 2,2-dimethoxypropane or equivalent reagents (e.g. 2-methoxypropene). However, when $R^1=R^2=R^3$ then $R^1=R^2=R^3$ cannot be —CH$_3$.

The compounds of Formula (II) may be supplied in a solution of 2,2-dimethoxypropane, which may also contain trace amounts of Amberlite 118-H$^+$ acid resin. The reaction generally takes place over a period of several hours. The reaction mixture may then be filtered, followed by evaporation of the solvent. The crude acetonides produced by the instant process of the present invention can be purified by any appropriate method.

The instant conversion reaction of silane cis-diols (the compound of Formula (II)) to the acetonide derivatives (the compound of Formula (III)) is illustrated in the diagram below.

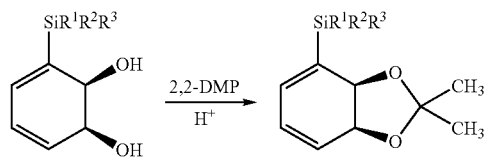

Confirmation of the identity of the acetonide derivative compounds may be obtained by analysis of $^1$H and $^{13}$C NMR spectra. The present invention includes the compounds produced by this transformation.

Examples of suitable cis-diol substrates and the corresponding acetonide derivatives are shown below in Scheme 2.

Scheme 2.
Acetonide derivatives of cis-diols

| cis-diol substrate | | Acetonide derivative | |
|---|---|---|---|
| 2a | 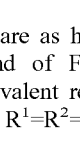 | 3a |  |
| 2b | 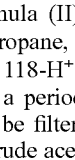 | 3b | 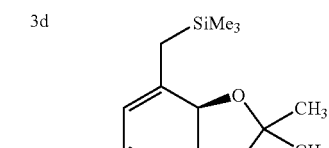 |

-continued

Scheme 2.
Acetonide derivatives of cis-diols

| cis-diol substrate | | Acetonide derivative | |
|---|---|---|---|
| 2c | 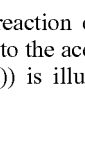 | 3c | 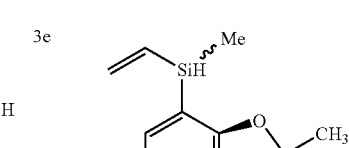 |
| 2d | 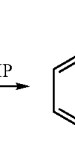 | 3d | 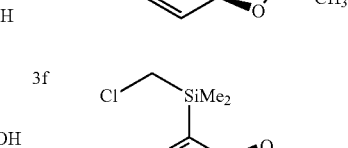 |
| 2e | 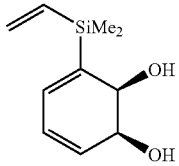 | 3e |  |
| 2f | 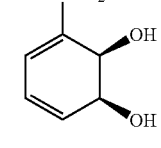 | 3f | 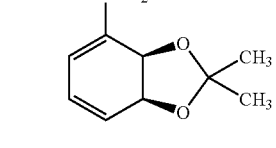 |

In accordance with one embodiment of the present invention, a compound of Formula (II') is converted into the more stable acetonide derivatives of the compound of Formula (III'):

Formula (III')

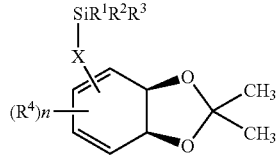

in which $R^1$, $R^2$, $R^3$, $R^4$, X, and n are as hereinbefore defined, by reaction of the compound of Formula (II') with 2,2-dimethoxypropane or equivalent reagents (e.g. 2-methoxypropene). However, when X=C$_2$ alkynyl and $R^1=R^2=R^3$ then $R^1=R^2=R^3$ cannot be —CH$_3$.

In accordance with one embodiment of the present invention, a compound of Formula (II") is converted into the more stable acetonide derivatives of the compound of Formula (III"):

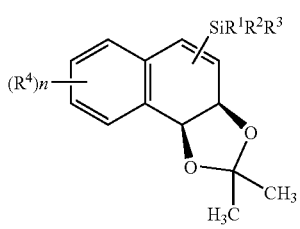

Formula (III″)

in which $R^1$, $R^2$, $R^3$, $R^4$, and n are as hereinbefore defined, by reaction of the compound of Formula (II″) with 2,2-dimethoxypropane or equivalent reagents (e.g. 2-methoxypropene).

In accordance with one embodiment of the present invention, a compound of Formula (II‴) is converted into the more stable acetonide derivatives of the compound of Formula (III‴):

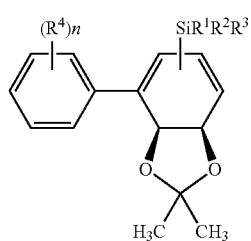

Formula (III‴)

in which $R^1$, $R^2$, $R^3$, $R^4$, and n are as hereinbefore defined, by reaction of the compound of Formula (II‴) with 2,2-dimethoxypropane or equivalent reagents (e.g. 2-methoxypropene).

In accordance with one embodiment of the present invention, a compound of Formula (II″″) is converted into the more stable acetonide derivatives of the compound of Formula (III″″):

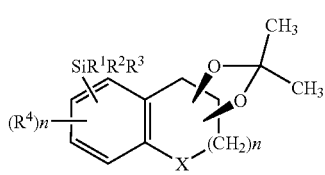

Formula (III″″)

in which $R^1$, $R^2$, $R^3$, $R^4$, X, and n are as hereinbefore defined, by reaction of the compound of Formula (II″″) with 2,2-dimethoxypropane or equivalent reagents (e.g. 2-methoxypropene).

In accordance with the present invention, further contemplated is the conversion of aryl silanes to catechols through the cis-diols. In accordance with one embodiment of the present invention an aryl silane of Formula (I) is converted to a catechol of Formula (IV) through the cis-diols compounds of Formula (II). The process results in the biocatalytic synthesis of a compound of Formula (IV):

Formula (IV)

in which $R^1$, $R^2$, and $R^3$ are as hereinbefore defined, by reaction of the compound of Formula (II) with a diol dehydrogenase enzyme. It is contemplated that a strain of *E. coli* possessing both the toluene dioxygenase gene as well as a diol dehydrogenase gene can be used to convert aryl silanes (the compounds of Formula (I)) to the corresponding catechols (the compounds of Formula (IV)). Suitable diol dehydrogenases may be found in E.C. 1.3.1.19. For example the plasmid TDTG602 which may have the gene todC12BAD may be used in accordance with the present invention. Suitable diol dehydrogenases are found in Zylstra, G. J. and Gibson, D. T., *Toluene degradation by Pseudomonas putida F1, Nucleotide sequence of the todC1C2BADE genes and their expression in Escherichia coli*, J. Biol. Chem. 264: 14940–14946 (1989), which is incorporated by reference herein.

Examples of suitable cis-diol substrates and the corresponding catechols are shown below in Scheme 3.

Scheme 3.
Conversion of silane cis-diols to silane catechols

| cis-diol substrate | Catechol derivative |
|---|---|
| 2a | 4a |
| 2b | 4b |

In accordance with one embodiment of the present invention an aryl silane of formula (I') is converted to a catechol of formula (IV') through the cis-diols compounds of Formula (II'). The process results in the biocatalytic synthesis of a compound of Formula (IV'):

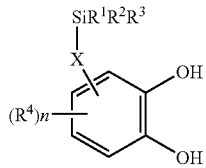

Formula (IV')

in which $R^1$, $R^2$, $R^3$, $R^4$, X, and n are as hereinbefore defined, by reaction of the compound of Formula (II') with a diol dehydrogenase enzyme.

In accordance with one embodiment of the present invention an aryl silane (I'') is converted to a catechol of formula (IV'') through the cis-diols compounds of Formula (II''). The process results in the biocatalytic synthesis of a compound of Formula (IV''):

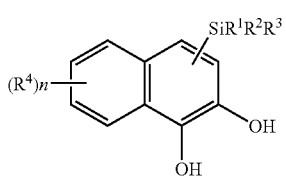

Formula (IV'')

in which $R^1$, $R^2$, $R^3$, $R^4$ and n are as hereinbefore defined, by reaction of the compound of Formula (II'') with a diol dehydrogenase enzyme.

In accordance with one embodiment of the present invention an aryl silane of formula (I''') is converted to a catechol of formula (IV''') through the cis-diols compounds of Formula (II'''). The process results in the biocatalytic synthesis of a compound of Formula (IV'''):

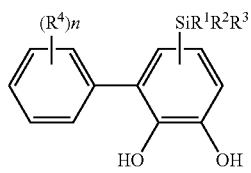

Formula (IV''')

in which $R^1$, $R^2$, $R^3$, $R^4$ and n are as hereinbefore defined, by reaction of the compound of Formula (II''') with a diol dehydrogenase enzyme.

In accordance with one embodiment of the present invention an aryl silane of Formula (I'''') is converted to a catechol of Formula (IV'''') through the cis-diols compounds of Formula (II''''). The process results in the biocatalytic synthesis of a compound of Formula (IV''''):

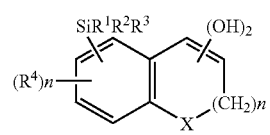

Formula (IV'''')

in which $R^1$, $R^2$, $R^3$, $R^4$, X and n are as hereinbefore defined, by reaction of the compound of Formula (II') with a diol dehydrogenase enzyme.

In accordance with the present invention, the transformation of additional aryl silanes to cis-diols, including bis-aryl silanes such as 2-(diphenylmethylsilyl)ethanol and the compounds produced thereby, is further contemplated. The oxidation of a single aryl ring will result in materials possessing chirality around the silicon atom, as well as two new stereogenic carbon centers.

In accordance with the present invention, further contemplated are additional chemical transformations of the cis-diols and acetonides of the present invention. In accordance with one aspect of the present invention, the cis-diol acetonides may be used to form cycloadducts by allowing the concentrated cis-diol acetonide to stand at room temperature. For example, Scheme 4 illustrates the formation of cycloadducts.

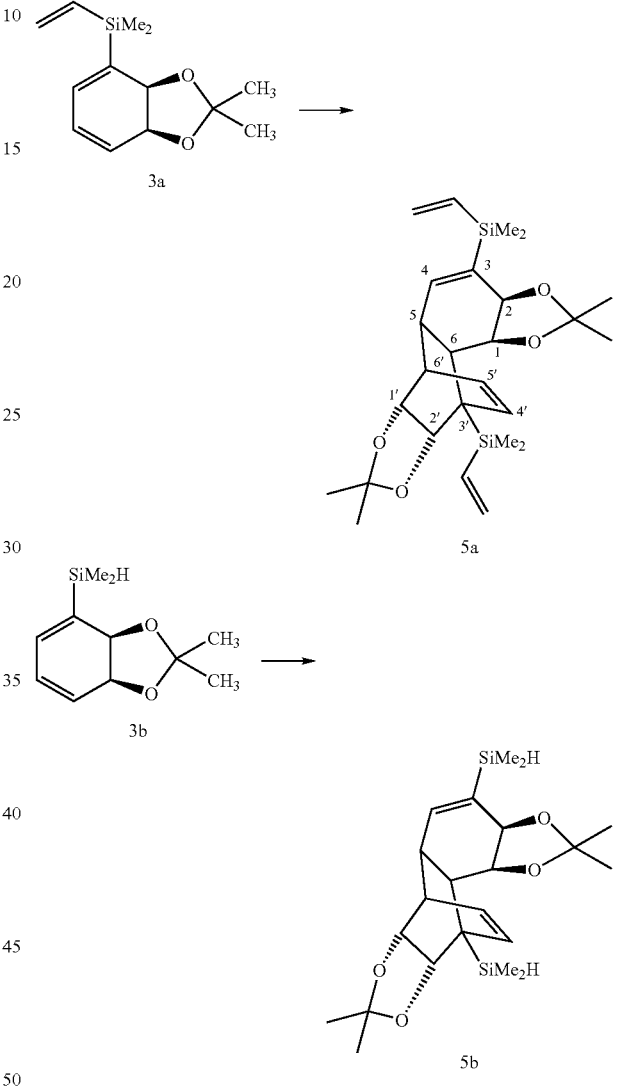

Scheme 4. Cycloadducts of silane cis-diol acetonides

It will be understood that the cis-diol acetonides of Formulas (III)–(III'''') may be used to form cycloadducts in accordance with the present invention.

In accordance with another aspect of the present invention the derivatization or reaction of the hydroxyl groups of the cis-diol is contemplated. Suitable methods for the derivatization and protection are detailed in T. W. Greene and P. G. M. Wits, Protective Groups in Organic Synthesis, $3^{rd}$ ed. (1999), Wiley, New York and is incorporated by reference herein. For example, as discussed above, the hydroxyl groups of the cis-diols may be derivatized to form the acetonides of Formulas (III–III''''). Additionally, the hydroxyl groups of the cis-diols may be derivatized using any alkylidene group in a manner similar to the formation of the acetonides. The alkylidene may be any suitable alkylidene. For example, the alkylidene may be benzyldene or ethylidene.

In another example, at least one of the hydroxyl groups of the cis-diol may be removed. For example, the cis-diols may be reacted to give phenols of the formula

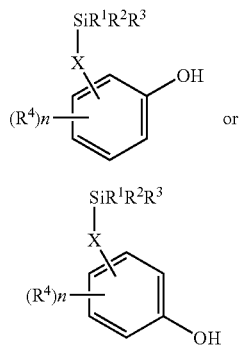

Formula (Va)

or

Formula (Vb)

wherein:
R$^1$, R$^2$, and R$^3$ are each independently selected from hydrogen, a halogen, aryl, a linear or branched C$_1$–C$_{18}$ alkyl, a linear or branched C2–C$_{18}$ alkenyl, a linear or branched C$_2$–C$_{18}$ alkynyl, halomethyl, OR, SR, NR$_{2-3}$, or O(CO)R;
R$^4$ is selected from hydrogen, a halogen, linear or branched C$_1$–C$_{18}$ alkyl, linear or branched C$_2$–C$_{18}$ alkenyl, linear or branched C$_2$–C$_{18}$ alkynyl, halomethyl, CF$_3$, CN, NO$_2$, SR, OR, NR$_{2-3}$, O(CO)R, SiR$^1$R$^2$R$^3$, or a bridging group between two arene or substituted arene moieties;
n is 0–3;
R is hydrogen, linear or branched C$_1$–C$_{18}$ alkyl, or SiR$^1$R$^2$R$^3$;
X is nothing, a divalent linear or branched C$_1$–C$_{18}$ alkyl, C$_2$–C$_{18}$ alkenyl, and C$_2$–C$_{18}$ alkynyl spacer.

However, when X=nothing then R$^1$, R$^2$, and R$^3$ cannot be R$^1$=R$^2$=CH$_3$ and R$^3$=H or R$^1$=R$^2$=R$^3$=CH$_3$.

For example, the derivatives may be of the formula

which may be made by reacting the appropriate cis-diol with H$^+$ in water.

In a further example, the hydroxyl groups of the cis-diols may be derivatized to form a di-O-acyl derivative. The acyl may be any suitable acyl functionality. For example, the acyl may be a linear or branched C$_1$–C$_{18}$ alkyl, a linear or branched C$_2$–C$_{18}$ alkenyl, or a linear or branched C$_2$–C$_{18}$ alkynyl. For example, the di-O-acyl derivative may be a derivative of the formula:

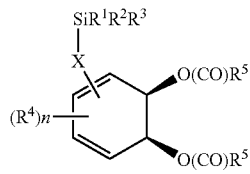

Formula (VI)

wherein:
R$^1$, R$^2$, and R$^3$ are each independently selected from hydrogen, a halogen, aryl, a linear or branched C$_1$–C$_{18}$ alkyl, a linear or branched C$_2$–C$_{18}$alkenyl, a linear or branched C$_2$–C$_{18}$ alkynyl, halomethyl, OR, SR, NR$_{2-3}$, or O(CO)R;
R$^4$ is selected from hydrogen, a halogen, linear or branched C$_1$–C$_{18}$ alkyl, linear or branched C$_2$–C$_{18}$ alkenyl, linear or branched C$_2$–C$_{18}$ alkynyl, halomethyl, CF$_3$, CN, NO$_2$, SR, OR, NR$_{2-3}$, O(CO)R, SiR$^1$R$^2$R$^3$, or a bridging group between two arene or substituted arene moieties;
n is 0–3;
R$^5$ is linear or branched C$_1$–C$_{18}$ alkyl, halomethyl, linear or branched C$_2$–C$_{18}$ alkenyl, or linear or branched C$_2$–C$_{18}$ alkynyl;
R is hydrogen, linear or branched C$_1$–C$_{18}$ alkyl, or SiR$^1$R$^2$R$^3$; and
X is nothing, a divalent linear or branched C$_1$–C$_{18}$ alkyl, C$_2$–C$_{18}$ alkenyl, and C$_2$–C$_{18}$ alkynyl spacer.

For example, the di-O-acyl may be

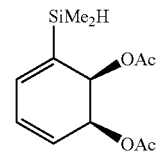

which may be made by reacting dimethylsilyl cyclohexadiene cis-diol (2b) with pyridine and acetic anhydride and then extracting the reaction mixture with ethyl acetate.

In yet another example, the hydroxyl groups of the cis-diol could be derivatized to form a silyl ether. For example, the silyl ether may be a derivative of the formula:

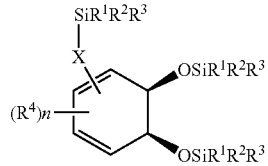

Formula (VII)

wherein:
R$^1$, R$^2$, and R$^3$ are each independently selected from hydrogen, a halogen, aryl, a linear or branched C$_1$–C$_{18}$ alkyl, a linear or branched C$_2$–C$_{18}$ alkenyl, a linear or branched C$_2$–C$_{18}$ alkynyl, halomethyl, OR, SR, NR$_{2-3}$, or O(CO)R;
R$^4$ is selected from hydrogen, a halogen, linear or branched C$_1$–C$_{18}$ alkyl, linear or branched C$_2$–C$_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–3;

R is hydrogen, linear or branched $C_1$–$C_{18}$ alkyl, or $SiR^1R^2R^3$; and

X is nothing, a divalent linear or branched $C_1$–$C_{18}$ alkyl, $C_2$–$C_{18}$ alkenyl, or $C_2$–$C_{18}$ alkynyl spacer.

For example, the silyl ether may be

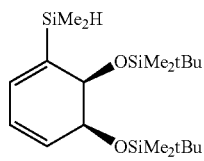

which may be made by reacting dimethylsilyl cyclohexadiene cis-diol (2b) with t-BuMe$_2$SiCl, dimethylformamide, and imidazole.

In a further example, the hydroxy groups of the cis-diols may be derivatized by forming a boronate ester. For example, the boronate ester may be an ester of the formula Formula (VIII)

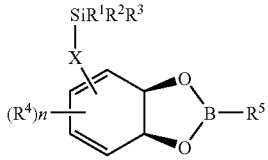

wherein:

$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;

$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–3;

$R^5$ is aryl, linear or branched $C_1$–$C_{18}$ alkyl, linear or branched $C_2$–$C_{18}$ alkenyl, or linear or branched $C_2$–$C_{18}$ alkynyl;

R is hydrogen, linear or branched $C_1$–$C_{18}$ alkyl, or $SiR^1R^2R^3$; and

X is nothing, a divalent linear or branched $C_1$–$C_{18}$ alkyl, $C_2$–$C_{18}$ alkenyl, and $C_2$–$C_{18}$ alkynyl spacer.

For example, the boronate ester may be

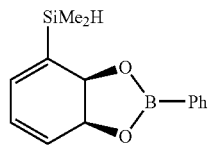

which may be made by reacting dimethylsilyl cyclohexadiene cis-diol (2b) with phenylboronic acid (PhB(OH)$_2$).

In accordance with another aspect of the present invention the oxidation of the double bonds of the cis-diols and acetonides of the present invention to the corresponding epoxy derivatives is contemplated. For example, the cis-diol may have the double bond oxidized to form epoxy derivatives of the formulas:

Formula (IXa)

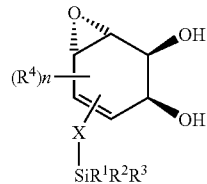

or

Formula (IXb)

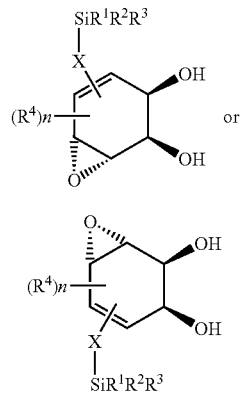

wherein:

$R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;

$R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;

n is 0–3;

R is hydrogen, linear or branched $C_1$–$C_{18}$ alkyl, or $SiR^1R^2R^3$; and

X is nothing, a divalent linear or branched $C_1$–$C_{18}$ alkyl, $C_2$–$C_{18}$ alkenyl, and $C_2$–$C_{18}$ alkynyl spacer.

For example, the epoxy derivatives may be

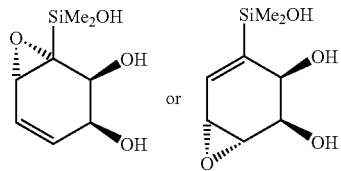

which may be made by reacting dimethylsilyl cyclohexadiene cis-diol (2b) with m-choloroperbenzoic acid (m-CPBA).

For example, the acetonides of the present invention may have the double bond oxidized to form epoxy derivatives of the formulas:

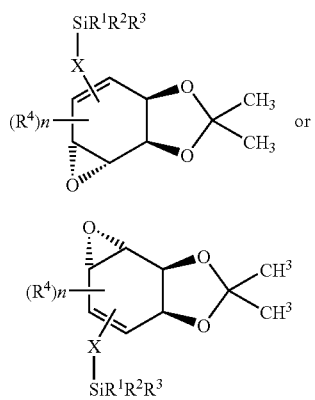

Formula (IXc)

or

Formula (IXd)

wherein:

R$^1$, R$^2$, and R$^3$ are each independently selected from hydrogen, a halogen, aryl, a linear or branched C$_1$–C$_{18}$ alkyl, a linear or branched C$_2$–C$_{18}$ alkenyl, a linear or branched C$_2$–C$_{18}$ alkynyl, halomethyl, OR, SR, NR$_{2-3}$, or O(CO)R;

R$^4$ is selected from hydrogen, a halogen, linear or branched C$_1$–C$_{18}$ alkyl, linear or branched C$_2$–C$_{18}$ alkenyl, linear or branched C$_2$–C$_{18}$ alkynyl, halomethyl, CF$_3$, CN, NO$_2$, SR, OR, NR$_{2-3}$, O(CO)R, SiR$^1$R$^2$R$^3$, or a bridging group between two arene or substituted arene moieties;

n is 0–3;

R is hydrogen, linear or branched C$_1$–C$_{18}$ alkyl, or SiR$^1$R$^2$R$^3$; and X is nothing, a divalent linear or branched C$_1$–C$_{18}$ alkyl, C$_2$–C$_{18}$ alkenyl, and C$_2$–C$_{18}$ alkynyl spacer.

However, when X=nothing then R$^1$, R$^2$, and R$^3$ cannot be R$^1$=R$^2$=R$^3$=CH$_3$.

For example, the epoxy derivatives may be

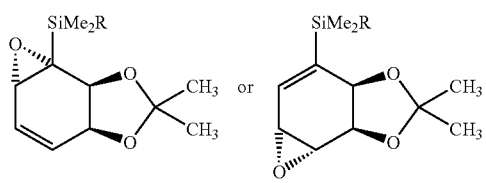

wherein R=H and OH.

which may be made by reacting dimethylsilyl cyclohexadiene cis-diol acetonide (3b) with m-CPBA.

In accordance with another aspect of the present invention the reduction of one or both of the double bonds of the cis-diols and acetonides of the present invention to the corresponding partially or fully saturated materials are contemplated. For example, the cis-diol may have at least one of the double bonds reduced to form partially or fully saturated material of the formulas:

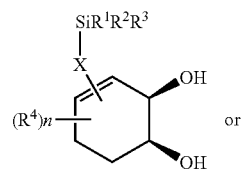

Formula (Xa)

or

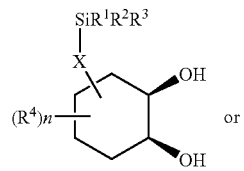

Formula (Xb)

or

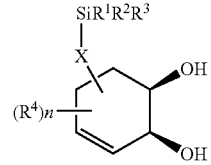

Formula (Xc)

wherein:

R$^1$, R$^2$, and R$^3$ are each independently selected from hydrogen, a halogen, aryl, a linear or branched C$_1$–C$_{18}$ alkyl, a linear or branched C$_2$–C$_{18}$ alkenyl, a linear or branched C$_2$–C$_{18}$ alkynyl, halomethyl, OR, SR, NR$_{2-3}$, or O(CO)R;

R$^4$ is selected from hydrogen, a halogen, linear or branched C$_1$–C$_{18}$ alkyl, linear or branched C$_2$–C$_{18}$ alkenyl, linear or branched C$_2$–C$_{18}$ alkynyl, halomethyl, CF$_3$, CN, NO$_2$, SR, OR, NR$_{2-3}$, O(CO)R, SiR$^1$R$^2$R$^3$, or a bridging group between two arene or substituted arene moieties;

n is 0–3;

R is hydrogen, linear or branched C$_1$–C$_{18}$ alkyl, or SiR$^1$R$^2$R$^3$; and X is nothing, a divalent linear or branched C$_1$–C$_{18}$ alkyl, C$_2$–C$_{18}$ alkenyl, and C$_2$–C$_{18}$ alkynyl spacer.

For example, the partially or fully saturated derivatives may be

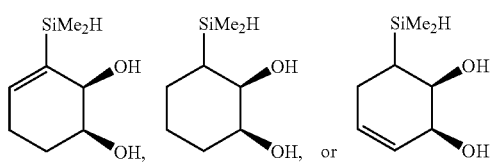

which may be made by exposing dimethylsilyl cyclohexadiene cis-diol (2b) to hydrogen gas or through the diimide procedure using potassium azodicarbonamide in acetic acid. (Pasto., D. J. "Reduction with Diimide" *Organic. Reactions,* 1991, 40, 91.)

For example, the acetonide may have at least one the double bonds reduced to form partially or fully saturated material of the formulas:

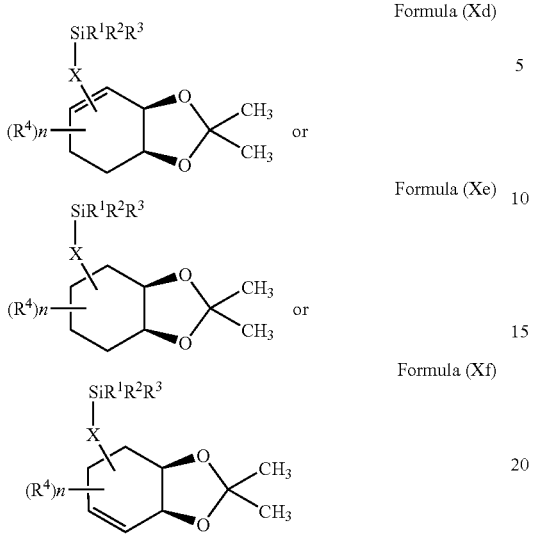

wherein:
- $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;
- $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;
- n is 0–3;
- R is hydrogen, linear or branched $C_1$–$C_{18}$ alkyl, or $SiR^1R^2R^3$; and
- X is nothing, a divalent linear or branched $C_1$–$C_{18}$ alkyl, $C_2$–$C_{18}$ alkenyl, and $C_2$–$C_{18}$ alkynyl spacer.

For example, the derivative may be

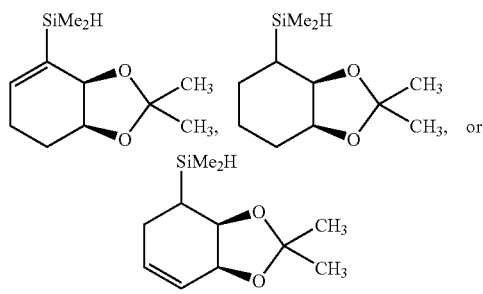

which may be made by exposing dimethylsilyl cyclohexadiene cis-diol acetonide (4b) to hydrogen gas or diimide.

In accordance with another aspect of the present invention, cis-diols and acetonides having a hydrosilane function may be derivatized by reacting the hydrosilane function. For example, the cis-diol or acetonide may have formulas of:

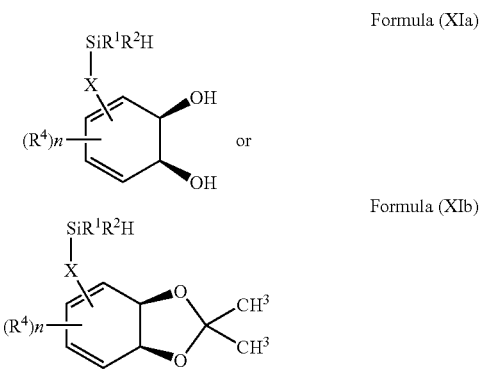

wherein:
- $R^1$ and $R^2$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;
- $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;
- n is 0–3;
- R is hydrogen, linear or branched $C_1$–$C_{18}$ alkyl, or $SiR^1R^2R^3$; and
- X is nothing, a divalent linear or branched $C_1$–$C_{18}$ alkyl, $C_2$–$C_{18}$ alkenyl, and $C_2$–$C_{18}$ alkynyl spacer.

For example, the cis-diol or acetonide having a hydrosilane function may by hydrolyzed to a corresponding silanol. For example, the cis-diol of Formula (XIa) may be hydrolyzed to a silanol of the formula

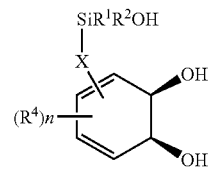

wherein $R^1$, $R^2$, $R^4$, X, and n are as defined above with respect to Formula (XIa). The acetonide of Formula (XIb) may be hydrolyzed to a silanol of the formula

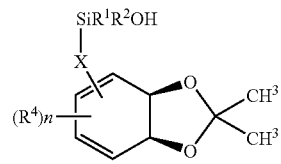

wherein $R^1$, $R^2$, $R^4$, X, and n are as defined above with respect to Formula (XIb). For example, the silanol may be

which may be made by reacting dimethylsilyl cyclohexadiene cis-diol (2b) with NaOH, ACN/H$_2$O. The silanol may be further condensed to form

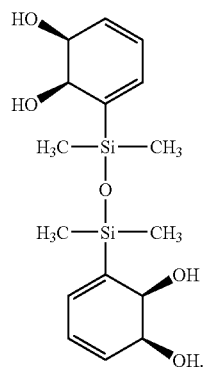

In a further example, the silanol may be

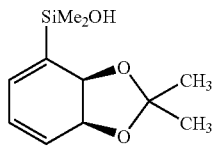

which may be made by reacting dimethylsilyl cyclohexadiene cis-diol acetonide (4b) with ACN and H$_2$O at a pH of greater than about 9. The silanol may be further condensed to form

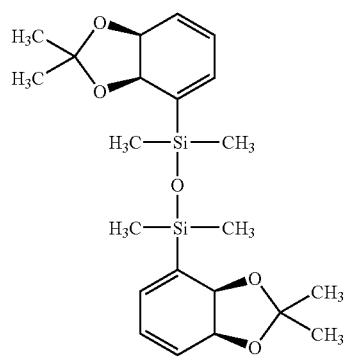

In another example, the cis-diol or acetonide having a hydrosilane function may be subject to alcoholysis to form an alkoxy derivative. For example, the cis-diol of Formula (XIa) or the acetonide of Formula (XIb) may be subject to alcoholysis to form a alkoxy derivatives of the formulas

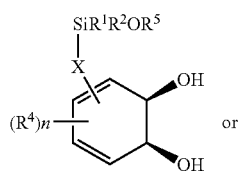

Formula (XIIIa)

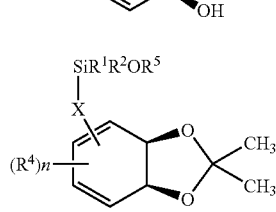

Formula (XIIIb)

wherein $R^1$, $R^2$, $R^4$, X, and n are as defined above with respect to Formulae (XIa, XIb), and $R^5$ is an aryl, a linear or branched $C_1$–$C_{18}$ alkyl, a linear or branched $C_2$–$C_{18}$ alkenyl, a linear or branched $C_2$–$C_{18}$ alkynyl. For example, the alkoxy derivative may be

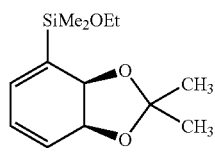

which may be made by reacting dimethylsilyl cyclohexadiene cis-diol acetonide with ethyl alcohol and sodium metal. In a further example, the alkoxy derivative may be

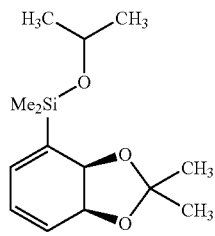

which may be made by reacting dimethylsilyl cyclohexadiene cis-diol acetonide with isopropyl alcohol and Pt(IV).

In a further example, the cis-diol or acetonide bearing either hydrosilane or vinylsilane functionality are subjected to hydrosilylation reactions resulting in the formation of a silicon-carbon bond.

Scheme 5 shown below illustrates a number of the reactions of dimethylsilyl cyclohexadiene cis-diol (2b) as discussed above.

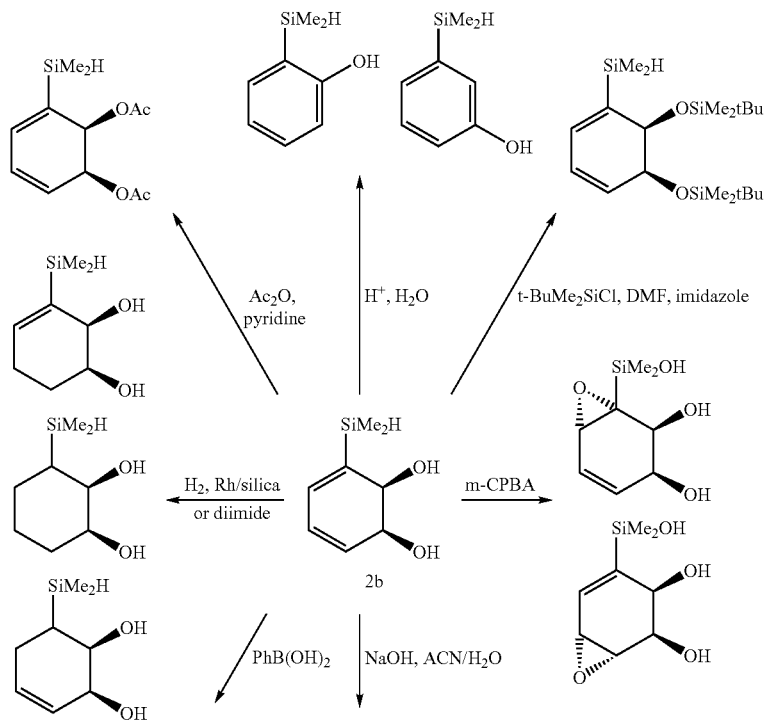
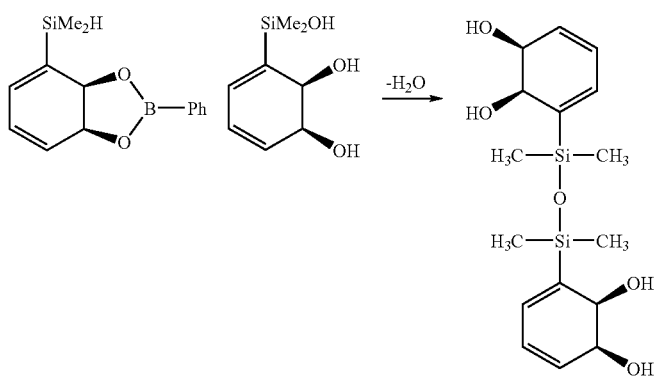

Scheme 6 shown below illustrates a number of the reactions of dimethylsilyl cyclohexadiene cis-diol acetonide (3b) discussed above.

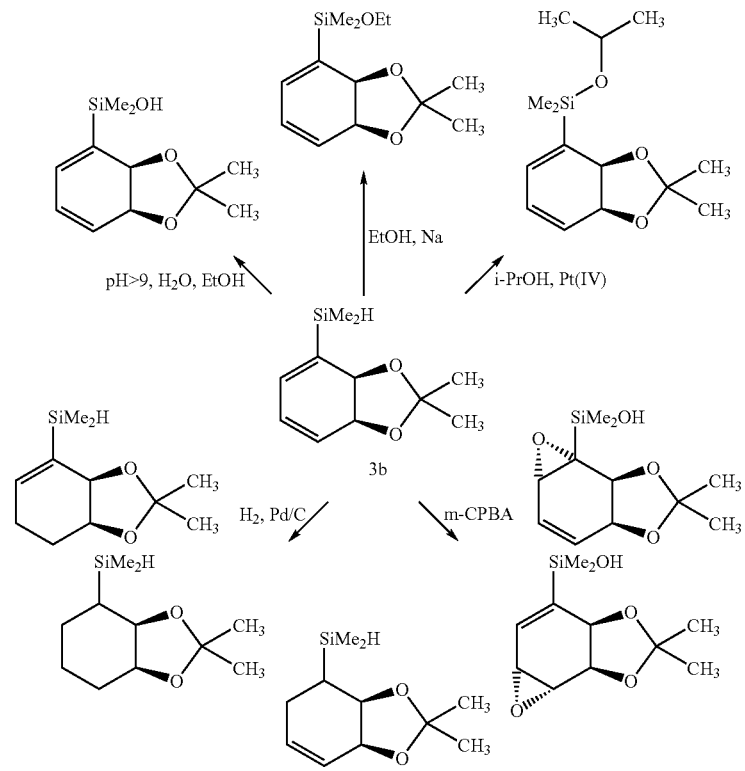

In order that the invention may be more readily understood, reference is made to the following examples, which are intended to be illustrative of the invention, but are not intended to be limiting in scope.

EXAMPLE 1

Conversion of the six aryl silanes illustrated in Scheme 1 to the corresponding cis-diols was done using *E. coli* strain JM109 (pDTG601) expressing the *P. putida* F1 toluene dioxygenase genes (todC1C2BA) (SEQ ID No. 1). Cells were grown in minimal salts broth (MSB) in either a shake flask or 14 L fermentor and harvested upon attaining OD 70 (Hudlicky, T. et al. (1999) *Organic Syntheses*, Vol. 76, 77). The cell mass was resuspended in 100 mM phosphate buffer having a pH of 7.4 and containing 5 g/L glucose to OD 35. Aryl silane substrates (1–20 g/L) were added and the mixtures were incubated at 37° C. at 225 rpm for 6 hours. The pH of the mixture was adjusted back up to pH 7.4 after an initial 2 hour incubation.

The whole broth was then centrifuged to remove the cells and the supernatant separated and extracted with ethyl acetate following saturation with sodium chloride. The organic extract was dried over sodium sulfate, filtered and concentrated under vacuum. The remaining material was subjected to 300 MHz NMR and GC/MS analysis to determine the extent of conversion to the cis-diol products. The products are illustrated above in Scheme 1.

The products were analyzed. Dimethylphenylvinylsilane cis-diol (2a) [(1S, 2S)-3-(dimethylvinylsilyl)cyclohexa-3,5-diene-1,2-diol] $^1$H NMR (300 MHz, $d_6$-DMSO) δ 6.21, dd, J=24.5, 14.4 Hz, H3'; 6.11, dt, J=1.6, 6.3 Hz H4; 5.96, dd, J=14.4, 4.1 Hz, H2'; 5.90, ddd, H5; 5.80, ddd, H6; 5.71, dd, J=24.5, 4.1 Hz, H1'; 4.02, m, H2; 3.96, m, H1; 0.18, s, 6H, SiMe. GC/MS: 178 [M-18]$^+$.

Dimethylphenylsilane cis-diol (2b) [[(1S, 2S)-3-(dimethylsilyl)cyclohexa-3,5-diene-1,2-diol] $^1$H NMR (300 MHz, $d_6$-DMSO) δ 6.27, dt, J=1.5, 6.3 Hz H4; 5.98, dd, J=14.4, 4.1 Hz, H5; 5.95, ddd, H6; 4.20, dd, J=10.5, 2.2 Hz, H1; 4.17, sept, J=6.0 Hz, SiH; 4.07, bdd, J=10.5, 6.0 Hz, H2; 0.21, d, 6H, SiMe. GC/MS: 152 [M-18]$^+$.

Phenyltrimethylsilane cis-diol (2c) [[(1S, 2S)-3-(trimethylsilyl)cyclohexa-3,5-diene-1,2-diol] $^1$H NMR (300 MHz, $d_6$-DMSO) δ 6.21, dt, J=5.0, 1.0 Hz H4; 5.97, ddd, J=9.5, 6.3, 1.4 Hz, H5; 5.88, dddd, H6; 4.06, m, 2H, H1, 2; 0.05, d, 6H, SiMe. GC/MS: 166 [M-18]$^+$.

Benzyltrimethylsilane cis-diol (2d) [[(1S, 2S)-3-(trimethylsilylmethyl)cyclohexa-3,5-diene-1,2-diol] $^1$H NMR (300 MHz, $d_6$-DMSO) δ 5.87, ddd, J=9.5, 5.3, 2.1 Hz, H5; 5.61, bdd, J=3.1 Hz, H6; 5.55, bdd, H4; 4.21, m, H1; 3.78, d, J=6.0 Hz, H2; 1.78, 1.68, 2d, J=13.6 Hz, SiCH$_2$; 0.04, s, 9H, SiMe. GC/MS: 180 [M-18]$^+$.

Methylphenylvinylsilane cis-diol (2e) [[(1S, 2S)-3-(methylvinylsilyl)cyclohexa-3,5-diene-1,2-diol] $^1$H NMR (300 MHz, $d_6$-DMSO) δ 6.27, m, (R,S)-H4; 6.21, 6.20, 2dd, J=20.1, 14.6 Hz, (R,S)-H3'; 6.08, 6.06, 2dd, J=14.6, 4.7 Hz; 6.03, m, 2H, (R,S)-H5, 6; 5.85, 5.84, 2dd, J=20.1, 4.5 Hz, (R,S)-H1'; 4.35, m, 2H, (R,S)-H2, SiH; 4.15, m, (R,S)-H1;

0.32, 0.31, 2d, J=3.6 Hz, SiMe. GC/MS: 164 [M-18]+. (Chloromethyl)dimethylphenylsilane cis-diol (2f) GC/MS: 166 [M-18]+.

EXAMPLE 2

The bioconversion of cis-diols was performed in a shake flask. Cells for transformation in shake flask were grown either in separate shake flask culture or in a 14L fermentor (see Example 3). For the shake flask, 0.5 L MSB media with ampicillin (100 μg/mL) in a 2.8 L baffled Fernbach flask was inoculated with 1 mL of a fresh seed culture of JM109 (pDTG601) or JM109 (pDTG602) placed in a orbital shaker/incubator (250 rpm, 37° C.). After 4–6 hours the cells were induced with IPTG (10 mg/L) and incubated an additional 6–8 hours until $OD_{600}$=1.0. For the 14L fermentor method, cells were harvested at $OD_{600}$=30–60. Cells were collected by centrifugation and resuspended in transformation buffer (200 mM phosphate buffer pH 7.0, 0.4% glucose) to $OD_{600}$=10. Tranformations were done in a baffled Erlenmeyer flask equipped with a vapor bulb (Hudlicky, T. et al. *Organic Syntheses*, Vol. 76, 77), with the substrates (0.88 mg/mL) being added directly to the broth or to the vapor bulb and contacted with the cells for 3–4 hours (300 rpm, 37° C.). The products were extracted from the whole broth with dichloromethane. The organic extract was dried over sodium sulfate, filtered and concentrated to give the cis-diol products as oils.

EXAMPLE 3

A scaled-up conversion of dimethylphenylvinylsilane to the corresponding cis-diol in a 14 L fermentor was performed. Dimethylphenylvinylsilane (1a) (25 g, 0.15 mol) was contacted with cells of an *E coli*. strain expressing the dioxygenase JM109(pDTG601) that had been grown in a 14 L stirred fermentor at pH 7.0 and 37° C. to an OD of over 20. The silane was introduced into the fermentor at a rate such as to not adversely alter the viability of the bacterial cells, typically at or below 1 mL/min. The extent of conversion was followed by $^1$H NMR and GC/MS analysis of samples drawn from the fermentor until no dimethylphenylvinylsilane was detected. At that point the broth was collected and the cells removed by centrifugation. The supernatant was passed through a 10K cutoff size exclusion filter and extracted three times with ethyl acetate (1 L). The combined organic extracts were dried over sodium sulfate, filtered and the solvent removed under reduced pressure to give the corresponding cis-diol (2a) as a dark oil (12 g, 40%).

In a similar manner to that described above dimethylphenylsilane (1b) (50 g, 0.37 mol) was converted to the cis-diol (2b) as a tan oil that slowly crystallized in the refrigerator (36 g, 64%).

In a similar manner to that described above benzyltrimethylsilane (1d) (25 g, 0.15 mol) was converted to the cis-diol (2d) (8 g, 22%).

The enantiomeric excess (% ee) and absolute configuration of purified diols cis-(1S,2S)-3-(dimethylvinylsilyl)cyclohexa-3,5-diene-1,2-diol (2a) and cis-(1S,2S)-3-(dimethylsilyl)cyclohexa-3,5-diene-1,2-diol (2b) is greater than 98% ee as determined by the $^1$H NMR method of Resnick et al. (Resnick, S. M.; Torok, D. S.; Gibson, D. T. *J. Am. Chem. Soc.* 1995, 60, 3546–3549).

EXAMPLE 4

The cis-diols (2a-e) were converted to acetonide derivatives (3a-e) as shown in Scheme 2. The cis-diols were converted to the more stable acetonide derivatives by treatment of a solution of the diol in 2,2-dimethoxypropane with a trace of Amberlite 118-H+ acid resin over several hours. Filtration of the reaction mixture was followed by evaporation of the solvent. The crude acetonides were purified on a silica gel column by elution with ethyl acetate/hexane (1:9). Analysis of the $^1$H and $^{13}$C NMR spectra confirmed the identity of the compounds.

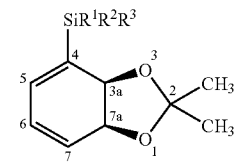

Dimethylphenylvinylsilane cis-diol acetonide (3a) [cis-4-(dimethylvinylsilyl)-2,2-dimethyl-3a,7a-dihydro-1,3-benzodioxazole] $^1$H NMR (300 MHz, CDCl$_3$) δ 6.21, dd, J=19.8, 14.7 Hz, H3'; 6.21, dt, J=5.3, 0.9 Hz, H5; 6.01, dd, J=14.7, 4.1 Hz, H2'; 5.99, ddd, J=9.3, 5.3, 1.0 Hz, H6; 5.87, ddd, J=9.3, 3.6, 1.0 Hz, H7; 5.74, dd, J=19.8, 4.4 Hz, H1'; 4.74, dd, J=9.0, 0.9 Hz, H3a; 4.59, ddd, J=9.0, 3.6, 1.0 Hz, H7a; 1.35, 1.31, 2s, 6H; 0.18, 2s, 6H, SiMe.

Dimethylphenylsilane cis-diol acetonide (3b) [cis-4-(dimethylsilyl)-2,2-dimethyl-3a,7a-dihydro-1,3-benzodioxazole] $^1$H NMR (300 MHz, CDCl$_3$) δ 6.23, bd, J=5.6 Hz, H5; 6.01, dd, J=9.8, 5.6 Hz, H6; 5.94, dd, J=9.8, 1.2 Hz, H7; 4.72, bd, J=9.0 Hz, H3a; 4.54, dd, J=9.0, 4.0 Hz, H7a; 4.12, sept, J=4.0 Hz, SiH; 1.37, 1.35, 2s, 6H; 0.21, 2d, 6H, SiMe.

Phenyltrimethylsilane cis-diol acetonide (3c) [cis-4-(trimethylsilyl)-2,2-dimethyl-3a,7a-dihydro-1,3-benzodioxazole] $^1$H NMR (300 MHz, CDCl$_3$) δ6.20, dt, J=5.6, 0.9 Hz, H5; 6.01, ddd, J=9.9, 5.4, 0.9 Hz, H6; 5.86, ddd, J=9.9, 3.8, 1.0 Hz, H7; 4.74, dd, J=9.0, 0.8 Hz, H3a; 4.59, ddd, J=9.0, 3.6, 0.8 Hz, H7a; 1.31, 1.36, 2d, 6H; 0.13, s, 9H, SiMe.

Methylphenylvinylsilane cis-diol acetonide (4d) [cis-4-[(R,S)-methylvinylsilyl]-2,2-dimethyl-3a,7a-dihydro-1,3-benzodioxazole] $^1$H NMR (300 MHz, CDCl$_3$) δ6.28, 6.25, 2bd, (R,S)-H5; 6.20, 6.19, 2ddd, J=19.1, 14.3, 1.7 Hz, (R,S)-H3'; 6.07, 6.05, 2dd, J=14.3, 4.3 Hz, (R,S)-H2'; 6.02, bdd, 9.6, 4.8 Hz, (R,S)-H6; 5.95, bddd, J=9.6, 3.9, 1.3 Hz, (R,S)-H7; 5.86, 5.85, 2ddd, J=19.6, 4.3, 3.6 Hz, (R,S)-H1'; 4.72, bdt, J=8.4, 1.1 Hz, (R,S)-H3a; 4.53, 4.52, 2dd, J=8.4, 2.1 Hz, (R,S)-H7a; 4.30, bdq, J=3.6 Hz, SiH; 1.38, 1.36, 2bs, 6H; 0.31, 2d, J=3.7 Hz, SiMe.

EXAMPLE 5

The conversion of cis-diols to catechol derivatives was performed. Conversion of cis-diols to the corresponding catechols was effected using *E. coli* strain JM109 (pDTG602) expressing the (+)-cis-(1S, 2R)-dihydroxy-3-methylcyclohexa-3,5-diene dehydrogenase gene (todD) from *Pseudomonas putida* F1. Transformations were conducted in a shake flask as described in Example 2. Dimethylphenylvinylsilane cis-diol (2a) or dimethylphenylsilane cis-diol (2b) was added directly to the re-suspended cells (1–2 mg diol/mL transformation broth) and incubated for 3–4 hours. The whole broth was extracted with ethyl acetate for analysis of the products. TLC: extracts of both transformations (silica gel, chloroform:acetone, 4:1) showed two UV-active bands at $R_f$≈0.4 and 0.6, the latter turning dark brown immediately after treatment with Gibbs reagent (0.1% 2, 6-dichloroquinone chlorimide in ethanol). GC/MS: 1-dimethylvinylsilyl-2,3-benezene diol (4a): m/z (rel. intensity) 194 (M+, 4%), 166 (100%); 1-dimethylsilyl-2,3-benzene diol (4b): m/z (rel. intensity) 168 (M+, 42%), 153 (96%), 75 (100%).

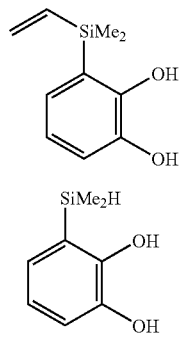

4a

4b

EXAMPLE 6

Cycloadducts (5a,b) of silane cis-diol acetonides as shown in Scheme 4 were produced. The dimethylphenylvinylsilyl cis-diol acetonide (3a) was found to form a novel product when left to stand at room temperature in concentrated form over the course of a week or more. Purification of the material by column chromatography on silica gel gave the cycloadduct (5a) as a colorless oil. $^1$H NMR (300 MHz, CDCl$_3$) δ 6.30, 6.18, 2dd, J=20, 14.4 Hz, 2H; 5.86–6.10, m, 5H; 7.72, 5.65, 2dd, J=20, 3.8 Hz, 2H; 4.18–4.28, m, 3H; 4.01, dd, J=5.2, 3.4 Hz, 1H; 2.90, m, H4; 2.38, bdd, J=8.7, 3.2 Hz, H4'; 2.05, bd, H5'; 1.32, 1.30, 1.23, 1.21, 4s, 12H; 0.24, 0.22, 0.16, 0.15, 4s, 12H, SiMe.

In the same manner as described above dimethylsilyl cis-diol acetonide (3b) was converted into the cycloadduct (5b). The material was purified as previously described to give a colorless oil. $^1$H NMR (300 MHz, CDCl$_3$); δ6.10, dd, J=4.0, 1.4 Hz, H4'; 6.04, bt, J=8 Hz, H5; 5.83, d, J=8 Hz, H4; 4.10–4.30, m, 4H; H1,2, 1',2'; 4.09, septuplet, 2H, J=3.8 Hz, SiH; 2.86, m, H6; 2.36, dd, J=9.0, 3.8 Hz, H5'; 2.18, bd, J=9.0 Hz, H6'; 1.25, 1.22, 1.21, 12H; 0.22, 0.21, 0.17, 3d, 12H, SiMe. GC/MS;

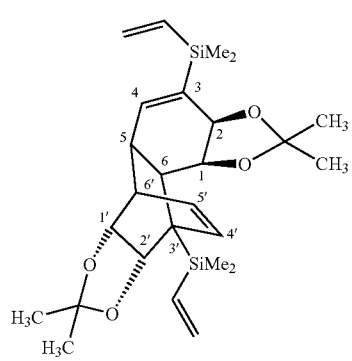

5a

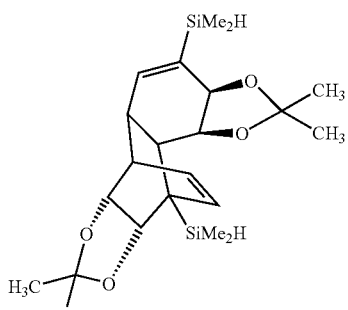

5b

EXAMPLE 7

Epoxy derivatives of the dimethylsilyl cis-diol acetonide (3b) as shown in Scheme 6 were produced. A solution of the acetonide (3b) (90 mg, 0.43 mmol) in dichloromethane (4 mL) was contacted with 2 mol equivalents of m-chloroperbenzoic acid (m-CPBA) at −10° C. After disappearance of the starting material (TLC), the reaction was extracted with saturated NaHCO$_3$ and the organic extract concentrated to give an oil. Purification on silica gel (hexane to hexane/EtOAc 2:1) gave a first a pair of epoxy hydrosilanes (6a, 7a, 2:1)(20 mg, 20%) followed by a pair of epoxy silanols (6b, 7b, 2:1)(41 mg, 39%). The 1,6-epoxy regioisomers were the major products. $^1$H NMR (300 MHz) 6a: δ 6.05, ddd, J=10.3, 6.2, 1.7 Hz, H5; 5.76, dm, J=10.3 Hz; H6; 4.70, bd, J=6.0 Hz, H2; 4.36, dt, J=7.2, 2.4 Hz, H1; 4.01, sept, J=3.9 Hz, SiH; 3.16, dt, J=6.6, 1.2 Hz, H4; 1.36, 2s, 6H; 0.2, 2s, 6H, SiMe. 6b: δ6.05, ddd, J=10.3, 6.2, 1.7 Hz, H5; 5.77, dm, J=10.3 Hz; H6; 4.76, bd, J=7.0 Hz, H2; 4.37, dt, J=7.2, 2.4 Hz, H1; 3.25, dt, J=6.6, 1.2 Hz, H4; 2.4–2.8, b, 1H, SiOH; 1.36, 2s, 6H; 0.28, 0.22, 2s, 6H, SiMe. 7a: δ6.31, dd, J=5.4, 1.7 Hz, H4; 4.73, dd, J=7.2, 2.4 Hz, H2; 4.54, dd, J=7.2, 1.8 Hz, H1; 4.11, sept, J=3.9 Hz, SiH; 3.55, dd, J=5.4, 1.9 Hz, H6; 3.29, td, J=5.4, 1.2 Hz, H5; 1.38, s, 6H; 0.2, 2s, 6H, SiMe. 7b: δ6.31, dd, J=5.4, 1.7 Hz, H4; 4.76, d, J=7.0 Hz, H2; 4.63, dd, J=7.0, 1.9 Hz, H1; 3.54, dd, J=5.4, 1.9 Hz, H6; 3.29, td, J=5.4, 1.2 Hz, H5; 2.4–2.8, b, 1H, SiOH; 1.39, 2s, 6H; 0.22, 0.21, 2s, 6H, SiMe.

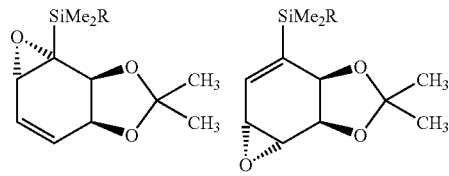

6a R = H; 6b R = OH 7a R = H, 7b R = OH

EXAMPLE 8

The dimethylsilyl cis-diol acetonide (3b) was reacted with sodium ethoxide. Freshly cut sodium (113 mg, 4.9 mmol) was added to anhydrous ethanol (freshly distilled from Mg) under an inert atmosphere. After all reaction had ceased, the solution was cooled in an ice/salt bath and the acetonide (3b) (155 mg, 0.74 mmol) was added. TLC soon after addition showed no starting material and a major product ($R_f$ 0.57, silica gel, hexanes:MTBE, 2:1, visualization: KMnO₄). The reaction was quenched with acetic acid (5.1 mmol), allowed to come to ambient temperature, diluted with dichloromethane, filtered and evaporated. ¹H-NMR showed a compound identified as the ethoxysilane (8) as shown below. ¹H NMR (300 MHz) δ 6.18, d, 1H; 5.9, m, 1H; 5.7, m, 1H; 4.7, d, 1H; 4.55, d, 1H; 1.6, m; 0.02, d, 6H.

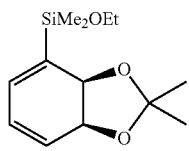

8

EXAMPLE 9

The dimethylsilyl cis-diol acetonide (3b) was reacted with isopropanol. A solution of the cis-diol acetonide (3b) (100 mg, 0.48 mmol) in isopropanol (3 mL) was treated with chloroplatinic acid (H₂PtCl₄, 0.005 mol %) at 50° C. over 24 h. TLC indicated the disappearance of the starting material and the formation of a new product. The reaction mixture was concentrated and purified on silica gel (ethyl acetate/hexane, 1:10) to give the isopropoxysilane (9) as a colorless oil. ¹H NMR (300 MHz, CDCl₃) δ6.32, bd, J=5.4 Hz, H5; 6.00, ddd, J=9.6, 5.4, 1.2 Hz, H6; 5.90, ddd, J=9.8, 3.6, 1.2 Hz, H7; 4.70, dd, J=8.8, 1.0 Hz, H3a; 4.59, ddd, J=8.8, 3.8, 1.2 Hz, H7a; 4.03, sept, J=6.2 Hz, Me₂CH; 1.37, 1.36, 2s, 6H; 1.14, 1.15, 2d, J=6.2 Hz, Me₂CH; 0.26, 0.24, 2s, 6H, SiMe.

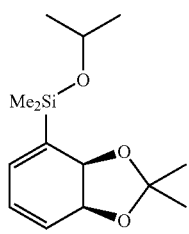

9

EXAMPLE 10

The hydrogenation of the dimethylsilyl cis-diol acetonide (3b) was performed. The acetonide (3b) (130 mg, 0.7 mmol) was dissolved in MTBE in a test tube. 5% rhodium on alumina (30 mg) was added and the mixture was hydrogenated on a Parr-shaker at 65 psi under hydrogen gas (H₂) for 24 hrs. The mixture was filtered through celite and dried under reduced pressure. Solvent exchange using 3 dissolution/dry-down cycles with deuterochloroform successfully purged the product of MTBE. Analysis by ¹H-NMR showed mostly the completely saturated analogue. Decoupling experiments demonstrated that the hydrosilane functionality was intact. GC/MS showed that the major component was the hexahydroaromatic: m+/e 199 (—CH₃), and 156 (—C₃H₆O). The products shown below were present.

10a

10b

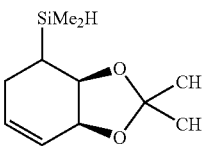

10c

EXAMPLE 11

The conversion of a cis-diol acetonide to the silanol (11) was performed. A solution of the acetonide (3b) (90 mg, 0.43 mmol) in DCM/ACN (4 mL, 1:1) was contacted with a 1 N NaOH solution (4 mL) with stirring over 2 h. TLC indicated the consumption of the starting material and the appearance of two new compounds. The reaction mixture was diluted with DCM (10 mL) and the organic layer isolated and washed with water and saturated brine solution. The organic extract was then dried over sodium sulfate, filtered and concentrated to give a mixture of the silanol (11a) and the disiloxane (11b) as an oil (65 mg, 4:1). ¹H NMR (300 MHz, CDCl₃) 1a: 6.23, dt, 1H; 6.04, dd, 1H; 5.95, ddd, 1H; 4.83, dd, 1H; 4.56, dd, 1H; 2.50, bs, 1H; 1.36, s, 6H: 0.26, 0.25, 2s, 6H. 11b: 6.26, dm, 1H; 5.97, m, 1H; 5.88, ddd, 1H; 4.71, dd, 1H; 4.56, m, 1H; 1.35, 2s, 6H: 0.22, s, 6H.

11a

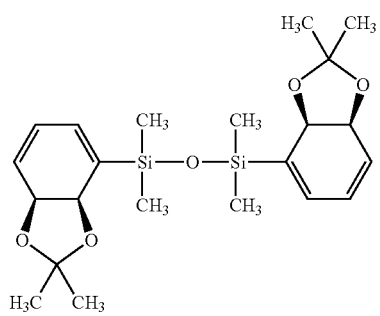

11b

EXAMPLE 12

The hydrosilylation of cis-diol acetonides may be performed. The cis-diol acetonides of this invention bearing either hydrosilane or vinylsilane functionality may be subjected to hydrosilylation reactions resulting in the formation of a silicon-carbon bond. For example the acetonide (3b) is contacted with an olefin and Wilkinsons catalyst [(Ph$_3$P)$_3$RhCl] in an appropriate solvent to yield a silane containing an additional silicon-carbon bond.

EXAMPLE 13

The reduction of the dimethylsilyl cyclohexadiene cis-diol 2b with diimide was performed. The diol (2b) was treated with diimide (N$_2$H$_2$) generated using freshly prepared potassium azodicarbonamide in acetic acid. Many products were observed on TLC. Column chromatography on silica gel using ether in hexanes yielded a small amount of crystalline material that was impure by $^1$H-NMR analysis. However, it appears that the major component was the 1,2,3,4-tetrahydrocyclohex-5-ene-1,2-Cis-diol (12). The silicon hydride appears to have been hydrolyzed, presumably to either the silanol or the disiloxane as shown below. $^1$H NMR (300 MHz): δ 5.83–5.91, d of p, 1H; 5.5–5.56, d of m, 1H; 4.17, bs, 1H; 4.06, bs, 1H; 3.92, sext., 1H.

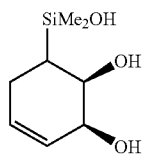

12

EXAMPLE 14

The hydrogenation of the dimethylsilyl cyclohexadiene cis-diol (2b) was performed. The diol (180 mg, 1 mmol) was hydrogenated over 5% rhodium on alumina (35 mg). After 24 hours, the mixture was filtered through celite and dried in vacuo. The $^1$H NMR spectrum showed what appeared to be the 1,2,5,6-tetrahydrocyclohex-3-ene (13a): 6.16 ppm, d of t. Some fully saturated material (13b) must also be present judging from the signal at 1.12 ppm, d of d, representing the methine hydrogen next to the silicon. Again, although more that 2 methyl signals are apparent, all are split, indicating that the hydrosilane groups are intact. The products are shown below.

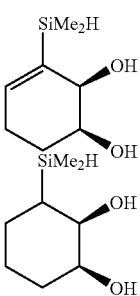

13a

13b

EXAMPLE 15

The acetylation of the dimethylsilyl cyclohexadiene cis-diol was performed. The dimethylsilyl cis-diol (2b) (370 mg, 2.1 mmol) was treated with pyridine (3 mL) and acetic anhydride (2 mL) at ice bath temperature for 30 minutes, and then for a further 2 hours a room temperature. The reaction mixture was diluted with water (50 mL) and extracted with ethyl acetate (2×20 mL). The organic extract was washed sequentially with saturated sodium bicarbonate solution and brine and dried over sodium sulfate. The extract was then filtered and concentrated with the aid of toluene to remove traces of pyridine and acetic acid. The residue was purified on a silica gel column (EtOAc/hexane, 1:9 to 2:3) to give the diacetate (14) as an oil as shown below. $^1$H NMR (300 MHz, d$_6$-DMSO): δ 6.42, dt, J=5.0, 1.5 Hz, H4; 6.22, ddd, J=9.2, 5.0, 1.2 Hz, H5; 6.01, ddd, J=9.2, 5.0, 1.2 Hz, H6; 5.56, dd, J=5.8, 2.3 Hz, H2; 5.36, ddd, J=5.8, 5.0, 1.2 Hz, H1; 4.36, sept, J=3.8 Hz, SiH; 2.01, 1.96, 2s, 6H, Ac; 0.29, d, 6H, SiMe.

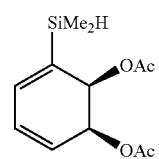

14

EXAMPLE 16

The dimethylsilyl cyclohexadiene cis-diol was converted to the silanol (15). A solution of the dimethylsilyl cis-diol (2b) (500 mg, 2.9 mmol) in a mixture of acetonitrile/water (5 mL, 4:1) was treated with 1 N sodium hydroxide (300 μL) at room temperature. A gas was immediately seen to form and TLC indicated the formation of a new lower Rf compound. Reverse phase chromatography on C18 silica gave the silanol (15) as a tan colored oil as shown below. $^1$H NMR (300 MHz, d$_6$-DMSO) δ 6.18, m, H4; 5.90, m, H5; 5.86, m, H6; 4.05, m, H2; 3.95, m, H1; 0.18, s, 6H, SiMe.

15

EXAMPLE 17

The silane cis-diols of this invention were converted to the meta- and/or ortho-phenols through contacting the cis-diols with acid in water or water/solvent mixtures. The phenolic products were readily detected on TLC with Gibb's reagent.

EXAMPLE 18

The hydrosilylation of hydro- and vinyl silane cis-diols may be performed. The cis-diols of this invention bearing either hydrosilane or vinylsilane functionality may be subjected to hydrosilylation reactions resulting in the formation of a silicon-carbon bond. For example the acetonide (2b) is contacted with an olefin and Wilkinsons catalyst [(Ph$_3$P)$_3$RhCl] in an appropriate solvent to yield a silane containing an additional silicon-carbon bond.

It will be obvious to those skilled in the art that various changes may be made without departing from the scope of the invention, which is not to be considered limited to what is described in the specification.

What is claimed is:

1. A compound comprising a cis-diol having the formula:

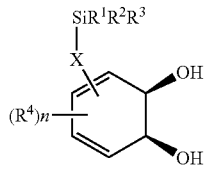

wherein:
- $R^1$, $R^2$, and $R^3$ are each independently selected from hydrogen, a halogen, aryl, a linear or branched $C_1$–$C_{18}$ alkyl, a linear or branched $C_2$–$C_{18}$ alkenyl, a linear or branched $C_2$–$C_{18}$ alkynyl, halomethyl, OR, SR, $NR_{2-3}$, or O(CO)R;
- $R^4$ is selected from hydrogen, a halogen, linear or branched $C_1$–$C_{18}$ alkyl, linear or branched $C_2$–$C_{18}$ alkenyl, linear or branched $C_2$–$C_{18}$ alkynyl, halomethyl, $CF_3$, CN, $NO_2$, SR, OR, $NR_{2-3}$, O(CO)R, $SiR^1R^2R^3$, or a bridging group between two arene or substituted arene moieties;
- n is 0–3;
- R is hydrogen, linear or branched $C_1$–$C_{18}$ alkyl, or $SiR^1R^2R^3$;
- X is a divalent linear or branched $C_1$–$C_{18}$ alkyl, $C_2$–$C_{18}$ alkenyl, or $C_2$–$C_{18}$ alkynyl spacer, except when X=$C_2$ alkynyl and $R^1$=$R^2$=$R^3$ then $R^1$=$R^2$=$R^3$ cannot be —$CH_3$.

2. The compound as claimed in claim 1 wherein:
- $R^1$, $R^2$, and $R^3$ are each independently selected from hydrogen, a linear or branched $C_1$–$C_5$ alkyl, a linear or branched $C_2$–$C_5$ alkenyl, a linear or branched $C_2$–$C_5$ alkynyl, halomethyl, or OR;
- $R^4$ selected from hydrogen, halogen, a linear or branched $C_1$–$C_5$ alkyl, a linear or branched $C_2$–$C_5$ alkenyl, a linear or branched $C_2$–$C_5$ alkynyl, CN, $NO_2$, OR or $SiR^1R^2R^3$;
- R is hydrogen, methyl, or ethyl; and
- X is either a divalent linear or branched $C_1$–$C_5$ alkyl, $C_2$–$C_5$ alkenyl, or $C_2$–$C_5$ alkynyl spacer.

3. The compound as claimed in claim 1 wherein:
- $R^1$, $R^2$, and $R^3$ are each independently selected from hydrogen, methyl, chloromethyl, or vinyl;
- $R^4$ selected from hydrogen, halogen, a linear or branched $C_1$–$C_3$ alkyl, a linear or branched $C_2$–$C_3$ alkenyl, a linear or branched $C_2$–$C_3$ alkynyl, CN, $NO_2$, OR or $SiR^1R^2R^3$.

4. The compound as claimed in claim 1 wherein said cis-diol comprises

* * * * *

SEQUENCE LISTING

<160> NUMBER OF SEQ ID NOS: 6

<210> SEQ ID NO 1
<211> LENGTH: 5033
<212> TYPE: DNA
<213> ORGANISM: Pseudomonas putida

<400> SEQUENCE: 1

```
gaattcgttc ggcggtgcct tgtctctggc ctttgctatc cgatttccgc atcgggttcg      60
ccgcctggtg ctgatgggtg ccgttggcgt gagcttcgag ctcacggatg gactggatgc     120
agtttggggt tatgagccgt ccgtgccgaa catgcgcaag gtcatggact acttcgccta     180
cgaccgaagt ctcgtttccg acgaactggc ggaactgcgc tacaaggcga gcacccggcc     240
cggttttcag gaggccttcg cttccatgtt ccctgctccg cggcagcgct gggtagatgc     300
gctggccagt tccgatcagg acatccggga catccggcat gaaacgctga tcctgcatgg     360
ccgcgacgat cgcgtgattc ccctcgaaac ctcgttgcgg ctgaaccagc tgatcgaacc     420
ctcccagtta catgtctttg gcaggtgtgg ccattgggtg cagatcgagc aaaaccgggg     480
ctttatccgc ttggtcaacg attttcttgc cgcggaggac tgatcgcaaa acgggaatg      540
accatccgtt ctgaaagcac gtcatcggca attgcctgcc aagtacccgc atccactac      600
cttgaaaagt gagaagacaa tgaatcagac cgacacatca cctatcaggc tgcgcaggag     660
ctggaacacc agcgagatag aagcgctctt tgacgagcat gccggacgta tcgatccgcg     720
catttatacc gatgaggatc tgtaccaact cgaactggag cgtgtcttcg cccggtcctg     780
gctgctgttg gggcatgaaa cccagattcg caagccgggc gattacatca cgacctacat     840
gggtgaagac cctgtcgtgg tcgtccggca gaaagacgcc agcattgccg tgttcctgaa     900
ccagtgccgc caccgtggca tgcgcatctg ccgcgcggat gccggaaacg cgaaggcgtt     960
cacttgcagc taccacgggt gggcttacga caccgccggc aatcttgtca atgtgcctta    1020
cgaggccgaa tccttcgcgt gcctgaacaa gaaggaatgg agcccgctga aggcccgggt    1080
agaaacctac aagggcctga ttttcgccaa ctgggatgag aacgctgtag acctcgacac    1140
gtatctgggc gaggcgaagt tctacatgga ccacatgctc gaccgcaccg aggccggcac    1200
cgaagcgatc ccgggcgtgc agaagtgggt cattccctgt aactggaaat cgccgcaga     1260
gcagttttgc agcgacatgt accatgccgg gacgacctcg catctgtctg gcatcctggc    1320
aggcctgcca gaagaccttg aaatggccga ccttgctccg ccgacagttg gcaagcagta    1380
ccgtgcgtca tggggcggac atggaagtgg cttctatgtc ggcgacccca atctgatgct    1440
tgccatcatg gggccaaagg tcaccagcta ctggaccgaa ggcccccgcgt cggaaaaggc    1500
ggccgaacgt ctgggtagcg tggagcgcgg ctcgaaactc atggtcgagc acatgaccgt    1560
cttccccacg tgttccttcc tcccaggtat caatacggtc cggacatggc atccgcgcgg    1620
gccgaacgag gtcgaggtat gggcgtttac ggtggtcgat gctgatgctc ctgacgatat    1680
caaggaagag ttccggcgcc agacgctgcg caccttctct gccggtggcg tgttcgagca    1740
ggacgacggg gagaactggg tcgagatcca gcacatcctg cgaggccaca ggcgcggagc    1800
cgcccttca atgccgagat gagcatggac cagaccgtcg acaacgaccc ggtttacccc    1860
gggcggatca gcaacaacgt ctacagcgag gaagctgccc gcgggctcta tgcccattgg    1920
ctgcggatga tgacatcccc cgactgggac gcgctgaagg cgacacgctg aatccagaga    1980
cagcttgcgc cacgcagtgg cgccggccag aggccgcatt tgacttcgac ccaggttgga    2040
```

-continued

```
tgcggtggac cttgtccatt tgaaatctac aaggaacgac catgattgat tcagccaaca   2100
gagccgacgt ctttctccgc aagccggcac ccgtagcgcc cgaactgcag cacgaagtcg   2160
agcagttcta ctattgggag ccaagcttc tcaacgatcg ccgcttcgag gagtggttcg    2220
cgctgctcgc ggaagacatt cactacttca tgcccattcg caccacgcgg atcatgcggg   2280
actcgcgcct tgaatactca ggctcccgag agtacgcgca cttcgatgac gacgccacga   2340
tgatgaaggg acgcttgcgc aagatcacgt ccgacgtgag ctggtccgag aaccccgcat   2400
cgcggacccg gcatctcgtg agcaacgtga tgatcgtcgg cgcagaggca gaaggggagt   2460
acgaaatctc aagcgccttc attgtgtacc gcaatcgtct ggagcggcag ctcgacatct   2520
ttgccggtga gcgtcgcgat acgttgcgcc gtaacacgag cgaggccggg ttcgagatcg   2580
tcaatcggac catcctgatc gaccagagca ccatcctggc caataacctc agtttcttct   2640
tctaggtgat gtcatgactt ggacatacat attgcggcag ggtgacctgc cacccggtga   2700
gatgcagcgc tacgaaggcg gcccggaacc tgtgatggtc tgcaacgtcg atggcgagtt   2760
cttcgcggtg caggatacct gcacgcatgg ggactgggcg ttgtcggatg gttacctgga   2820
cggtgatatt gtcgaatgca cgttgcattt cggcaagttc tgcgtgcgga ccgggaaggt   2880
gaaggcgctg cctgcttgca aacctatcaa ggtattccca atcaaggtcg aaggcgatga   2940
agtgcacgtc gatctcgaca acggggagtt gaagtgatgg ctacccatgt ggcgatcatc   3000
ggcaatggcg tgggtggctt cacgaccgcg caggccctac gtgccgaggg cttcgagggg   3060
agaatctcgc tgattgggga cgaaccgcat ctcccctatg accgaccatc cttgtccaag   3120
gcggttctcg acggcagcct tgagcggccc ccatactgg ccgaggccga ttggtacggc    3180
gaggcccgca tcgacatgct gaccggcccg gaagtcactg cccttgatgt gcagacaagg   3240
acgatcagtc tggatgatgg caccacgctc tctgcggacg ccatcgtcat cgcgacgggc   3300
agtcgagcgc ggacgatggc gttgcccggc agccaactgc ccggcgtcgt aacgctgcgc   3360
acctacggtg acgtgcaggt attgcgcgat agttggactt ccgcgacgcg gctgctgatt   3420
gtgggtggcg gattgatcgg ctgcgaggtc gcgacgacgg cgcgcaagct cggcctgtcg   3480
gtcacgatcc tggaggcagg tgatgaactg ctggtccgag tacttgggcg gcgtatcggt   3540
gcctggctgc gcggcctgct gacagaactt ggtgtgcagg tcgagttggg aacgggtgtc   3600
gtaggttttt ctggtgaggg ccagctcgaa caagtcatgg ccagcgatgg gcgcagcttc   3660
gtagccgata gcgcactcat ttgcgtcggc gcggagcccg cggatcaact tgcgcgtcaa   3720
gcgggcttgg catgtgaccg cggcgtcatt gtcgatcact gcggtgcgac gcttgccaaa   3780
ggcgtattcg ccgtcggaga tgtggccagt tggccgctgc gcgccggcgg ccggcgttcg   3840
ctcgaaacct atatgaacgc gcagcgccaa gccgccgcgg tggctgcggc cattctgggg   3900
aaaaacgtat cggcaccgca actgcccgtg tcctggacgg agatcgctgg gcatcgcatg   3960
cagatggcgg gcgatatcga aggacctggt gatttcgtct cgcgcggcat gcccggtagt   4020
ggcgctgccc tgttgttccg cctgcaggag cgaaggattc aggcggtcgt cgcggtcgat   4080
gcaccccgtg acttcgcgct tgcaacccga ttggtagaag cccgcgcggc aatcgagcca   4140
gcacggctgg cagatctttc aaacagtatg cgcgattttg ttcgtgcgaa tgaaggagac   4200
ctaacgtgag acttgaaggc gaagtggcct tggtgacagg cggtggcgca ggcctgggca   4260
gagcgatcgt ggatcgttat gtcgcggaag gtgcgcgtgt cgcggtgctg ataaatccg    4320
cggcaggcct ggaagcgctc aggaaactcc atggcgatgc aatcgtgggc gtggagggg    4380
```

-continued

```
atgttcgctc gctcgacagc catcgtgagg ctgtggcccg ctgcgtcgaa gcgttcggca    4440
agctggactg cctggttggc aatgctggcg tttgggacta cctgacccaa ctggtggata    4500
ttcccgacga cctcatatcg gaggcattcg aggaaatgtt cgaggtcaat gtcaagggct    4560
acatcctggc ggcaaaggct gcgctacctg cgctttatca gagcaaaggc agcgcgatat    4620
tcactgtgtc gaatgccggt ttctacccgg gcggtggcgg tgttctgtat acagctggca    4680
aacatgccgt gattggattg atcaagcagc tcgcgcacga tgggggccg cgtatccgcg     4740 tcaacggcat cgccccggt ggcattttgg ggagcgatct gcgcgggctg aagagccttg     4800
atttacaaga caagagcatt tcgacctttc cattggacga catgctgaaa tccgttcttc    4860
cgaccgggcg ggccgccact gccgaggaat acgccggcgc ctatgtcttc ttcgcgacgc    4920
gcggcgacac ggttccgctc accggtagcg tgttgaactt cgatggcggc atgggcgtgc    4980
gtggcttgtt cgaagccagc ctaggcgcac agctcgacaa gcacttcggt tga          5033
```

<210> SEQ ID NO 2
<211> LENGTH: 450
<212> TYPE: PRT
<213> ORGANISM: Pseudomonas putida

<400> SEQUENCE: 2

```
Met Asn Gln Thr Asp Thr Ser Pro Ile Arg Leu Arg Arg Ser Trp Asn
  1               5                  10                  15

Thr Ser Glu Ile Glu Ala Leu Phe Asp Glu His Ala Gly Arg Ile Asp
             20                  25                  30

Pro Arg Ile Tyr Thr Asp Glu Asp Leu Tyr Gln Leu Glu Leu Glu Arg
         35                  40                  45

Val Phe Ala Arg Ser Trp Leu Leu Leu Gly His Glu Thr Gln Ile Arg
     50                  55                  60

Lys Pro Gly Asp Tyr Ile Thr Thr Tyr Met Gly Glu Asp Pro Val Val
 65                  70                  75                  80

Val Val Arg Gln Lys Asp Ala Ser Ile Ala Val Phe Leu Asn Gln Cys
                 85                  90                  95

Arg His Arg Gly Met Arg Ile Cys Arg Ala Asp Ala Gly Asn Ala Lys
            100                 105                 110

Ala Phe Thr Cys Ser Tyr His Gly Trp Ala Tyr Asp Thr Ala Gly Asn
        115                 120                 125

Leu Val Asn Val Pro Tyr Glu Ala Glu Ser Phe Ala Cys Leu Asn Lys
    130                 135                 140

Lys Glu Trp Ser Pro Leu Lys Ala Arg Val Glu Thr Tyr Lys Gly Leu
145                 150                 155                 160

Ile Phe Ala Asn Trp Asp Glu Asn Ala Val Asp Leu Asp Thr Tyr Leu
                165                 170                 175

Gly Glu Ala Lys Phe Tyr Met Asp His Met Leu Asp Arg Thr Glu Ala
            180                 185                 190

Gly Thr Glu Ala Ile Pro Gly Val Gln Lys Trp Val Ile Pro Cys Asn
        195                 200                 205

Trp Lys Phe Ala Ala Glu Gln Phe Cys Ser Asp Met Tyr His Ala Gly
    210                 215                 220

Thr Thr Ser His Leu Ser Gly Ile Leu Ala Gly Leu Pro Glu Asp Leu
225                 230                 235                 240

Glu Met Ala Asp Leu Ala Pro Pro Thr Val Gly Lys Gln Tyr Arg Ala
                245                 250                 255

Ser Trp Gly Gly His Gly Ser Gly Phe Tyr Val Gly Asp Pro Asn Leu
```

```
                    260                 265                 270
Met Leu Ala Ile Met Gly Pro Lys Val Thr Ser Tyr Trp Thr Glu Gly
            275                 280                 285

Pro Ala Ser Glu Lys Ala Ala Glu Arg Leu Gly Ser Val Glu Arg Gly
        290                 295                 300

Ser Lys Leu Met Val Glu His Met Thr Val Phe Pro Thr Cys Ser Phe
305                 310                 315                 320

Leu Pro Gly Ile Asn Thr Val Arg Thr Trp His Pro Arg Gly Pro Asn
                325                 330                 335

Glu Val Glu Val Trp Ala Phe Thr Val Val Asp Ala Asp Ala Pro Asp
            340                 345                 350

Asp Ile Lys Glu Glu Phe Arg Arg Gln Thr Leu Arg Thr Phe Ser Ala
        355                 360                 365

Gly Gly Val Phe Glu Gln Asp Asp Gly Glu Asn Trp Val Glu Ile Gln
    370                 375                 380

His Ile Leu Arg Gly His Lys Ala Arg Ser Arg Pro Phe Asn Ala Glu
385                 390                 395                 400

Met Ser Met Asp Gln Thr Val Asp Asn Asp Pro Val Tyr Pro Gly Arg
                405                 410                 415

Ile Ser Asn Asn Val Tyr Ser Glu Glu Ala Ala Arg Gly Leu Tyr Ala
            420                 425                 430

His Trp Leu Arg Met Met Thr Ser Pro Asp Trp Asp Ala Leu Lys Ala
        435                 440                 445

Thr Arg
    450

<210> SEQ ID NO 3
<211> LENGTH: 187
<212> TYPE: PRT
<213> ORGANISM: Pseudomonas putida

<400> SEQUENCE: 3

Met Ile Asp Ser Ala Asn Arg Ala Asp Val Phe Leu Arg Lys Pro Ala
1               5                   10                  15

Pro Val Ala Pro Glu Leu Gln His Glu Val Glu Gln Phe Tyr Tyr Trp
            20                  25                  30

Glu Ala Lys Leu Leu Asn Asp Arg Arg Phe Glu Trp Phe Ala Leu
        35                  40                  45

Leu Ala Glu Asp Ile His Tyr Phe Met Pro Ile Arg Thr Thr Arg Ile
    50                  55                  60

Met Arg Asp Ser Arg Leu Glu Tyr Ser Gly Ser Arg Glu Tyr Ala His
65                  70                  75                  80

Phe Asp Asp Asp Ala Thr Met Met Lys Gly Arg Leu Arg Lys Ile Thr
                85                  90                  95

Ser Asp Val Ser Trp Ser Glu Asn Pro Ala Ser Arg Thr Arg His Leu
            100                 105                 110

Val Ser Asn Val Met Ile Val Gly Ala Glu Ala Glu Gly Tyr Glu
        115                 120                 125

Ile Ser Ser Ala Phe Ile Val Tyr Arg Asn Arg Leu Glu Arg Gln Leu
    130                 135                 140

Asp Ile Phe Ala Gly Glu Arg Arg Asp Thr Leu Arg Arg Asn Thr Ser
145                 150                 155                 160

Glu Ala Gly Phe Glu Ile Val Asn Arg Thr Ile Leu Ile Asp Gln Ser
                165                 170                 175
```

```
Thr Ile Leu Ala Asn Asn Leu Ser Phe Phe Phe
            180                 185
```

<210> SEQ ID NO 4
<211> LENGTH: 107
<212> TYPE: PRT
<213> ORGANISM: Pseudomonas putida

<400> SEQUENCE: 4

```
Met Thr Trp Thr Tyr Ile Leu Arg Gln Gly Asp Leu Pro Pro Gly Glu
  1               5                  10                  15

Met Gln Arg Tyr Glu Gly Gly Pro Glu Pro Val Met Val Cys Asn Val
             20                  25                  30

Asp Gly Glu Phe Phe Ala Val Gln Asp Thr Cys Thr His Gly Asp Trp
         35                  40                  45

Ala Leu Ser Asp Gly Tyr Leu Asp Gly Asp Ile Val Glu Cys Thr Leu
     50                  55                  60

His Phe Gly Lys Phe Cys Val Arg Thr Gly Lys Val Lys Ala Leu Pro
 65                  70                  75                  80

Ala Cys Lys Pro Ile Lys Val Phe Pro Ile Lys Val Glu Gly Asp Glu
                 85                  90                  95

Val His Val Asp Leu Asp Asn Gly Glu Leu Lys
            100                 105
```

<210> SEQ ID NO 5
<211> LENGTH: 408
<212> TYPE: PRT
<213> ORGANISM: Pseudomonas putida

<400> SEQUENCE: 5

```
Met Ala Thr His Val Ala Ile Ile Gly Asn Gly Val Gly Gly Phe Thr
  1               5                  10                  15

Thr Ala Gln Ala Leu Arg Ala Glu Gly Phe Glu Gly Arg Ile Ser Leu
             20                  25                  30

Ile Gly Asp Glu Pro His Leu Pro Tyr Asp Arg Pro Ser Leu Ser Lys
         35                  40                  45

Ala Val Leu Asp Gly Ser Leu Glu Arg Pro Pro Ile Leu Ala Glu Ala
     50                  55                  60

Asp Trp Tyr Gly Glu Ala Arg Ile Asp Met Leu Thr Gly Pro Glu Val
 65                  70                  75                  80

Thr Ala Leu Asp Val Gln Thr Arg Thr Ile Ser Leu Asp Asp Gly Thr
             85                  90                  95

Thr Leu Ser Ala Asp Ala Ile Val Ile Ala Thr Gly Ser Arg Ala Arg
            100                 105                 110

Thr Met Ala Leu Pro Gly Ser Gln Leu Pro Gly Val Thr Leu Arg
        115                 120                 125

Thr Tyr Gly Asp Val Gln Val Leu Arg Asp Ser Trp Thr Ser Ala Thr
        130                 135                 140

Arg Leu Leu Ile Val Gly Gly Leu Ile Gly Cys Glu Val Thr Ala
145                 150                 155                 160

Arg Lys Leu Gly Leu Ser Val Thr Ile Leu Glu Ala Gly Asp Glu Leu
                165                 170                 175

Leu Val Arg Val Leu Gly Arg Arg Ile Gly Ala Trp Leu Arg Gly Leu
            180                 185                 190

Leu Thr Glu Leu Gly Val Gln Val Glu Leu Gly Thr Gly Val Val Gly
        195                 200                 205
```

```
Phe Ser Gly Glu Gly Gln Leu Glu Gln Val Met Ala Ser Asp Gly Arg
    210                 215                 220

Ser Phe Val Ala Asp Ser Ala Leu Ile Cys Val Gly Ala Glu Pro Ala
225                 230                 235                 240

Asp Gln Leu Ala Arg Gln Ala Gly Leu Ala Cys Asp Arg Gly Val Ile
                245                 250                 255

Val Asp His Cys Gly Ala Thr Leu Ala Lys Gly Val Phe Ala Val Gly
            260                 265                 270

Asp Val Ala Ser Trp Pro Leu Arg Ala Gly Gly Arg Ser Leu Glu
        275                 280                 285

Thr Tyr Met Asn Ala Gln Arg Gln Ala Ala Val Ala Ala Ile
    290                 295                 300

Leu Gly Lys Asn Val Ser Ala Pro Gln Leu Pro Val Ser Trp Thr Glu
305                 310                 315                 320

Ile Ala Gly His Arg Met Gln Met Ala Gly Asp Ile Glu Gly Pro Gly
                325                 330                 335

Asp Phe Val Ser Arg Gly Met Pro Gly Ser Gly Ala Ala Leu Leu Phe
            340                 345                 350

Arg Leu Gln Glu Arg Arg Ile Gln Ala Val Val Ala Val Asp Ala Pro
        355                 360                 365

Arg Asp Phe Ala Leu Ala Thr Arg Leu Val Glu Ala Arg Ala Ala Ile
370                 375                 380

Glu Pro Ala Arg Leu Ala Asp Leu Ser Asn Ser Met Arg Asp Phe Val
385                 390                 395                 400

Arg Ala Asn Glu Gly Asp Leu Thr
                405

<210> SEQ ID NO 6
<211> LENGTH: 275
<212> TYPE: PRT
<213> ORGANISM: Pseudomonas putida

<400> SEQUENCE: 6

Met Arg Leu Glu Gly Glu Val Ala Leu Val Thr Gly Gly Ala Gly
1               5                   10                  15

Leu Gly Arg Ala Ile Val Asp Arg Tyr Val Ala Glu Gly Ala Arg Val
                20                  25                  30

Ala Val Leu Asp Lys Ser Ala Ala Gly Leu Glu Ala Leu Arg Lys Leu
            35                  40                  45

His Gly Asp Ala Ile Val Gly Val Glu Gly Asp Val Arg Ser Leu Asp
        50                  55                  60

Ser His Arg Glu Ala Val Ala Arg Cys Val Glu Ala Phe Gly Lys Leu
65                  70                  75                  80

Asp Cys Leu Val Gly Asn Ala Gly Val Trp Asp Tyr Leu Thr Gln Leu
                85                  90                  95

Val Asp Ile Pro Asp Asp Leu Ile Ser Glu Ala Phe Glu Glu Met Phe
            100                 105                 110

Glu Val Asn Val Lys Gly Tyr Ile Leu Ala Ala Lys Ala Ala Leu Pro
        115                 120                 125

Ala Leu Tyr Gln Ser Lys Gly Ser Ala Ile Phe Thr Val Ser Asn Ala
    130                 135                 140

Gly Phe Tyr Pro Gly Gly Gly Val Leu Tyr Thr Ala Gly Lys His
145                 150                 155                 160

Ala Val Ile Gly Leu Ile Lys Gln Leu Ala His Glu Trp Gly Pro Arg
                165                 170                 175
```

```
Ile Arg Val Asn Gly Ile Ala Pro Gly Gly Ile Leu Gly Ser Asp Leu
            180                 185                 190

Arg Gly Leu Lys Ser Leu Asp Leu Gln Asp Lys Ser Ile Ser Thr Phe
        195                 200                 205

Pro Leu Asp Asp Met Leu Lys Ser Val Leu Pro Thr Gly Arg Ala Ala
    210                 215                 220

Thr Ala Glu Glu Tyr Ala Gly Ala Tyr Val Phe Phe Ala Thr Arg Gly
225                 230                 235                 240

Asp Thr Val Pro Leu Thr Gly Ser Val Leu Asn Phe Asp Gly Gly Met
            245                 250                 255

Gly Val Arg Gly Leu Phe Glu Ala Ser Leu Gly Ala Gln Leu Asp Lys
            260                 265                 270

His Phe Gly
        275
```